(12) United States Patent
Vasudevan et al.

(10) Patent No.: US 8,859,546 B2
(45) Date of Patent: Oct. 14, 2014

(54) PICOLINAMIDE INHIBITORS OF KINASES

(75) Inventors: Anil Vasudevan, Union Grove, WI (US);
Thomas D. Penning, Elmhurst, IL (US);
Marina Pliushchev, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 355 days.

(21) Appl. No.: 13/354,556

(22) Filed: Jan. 20, 2012

(65) Prior Publication Data
US 2012/0190681 A1 Jul. 26, 2012

Related U.S. Application Data

(60) Provisional application No. 61/434,998, filed on Jan. 21, 2011.

(51) Int. Cl.
| | | |
|---|---|---|
| A61K 31/496 | (2006.01) | |
| C07D 401/14 | (2006.01) | |
| A61K 31/5377 | (2006.01) | |
| C07D 401/12 | (2006.01) | |
| C07D 413/14 | (2006.01) | |
| C07D 409/12 | (2006.01) | |
| C07D 413/12 | (2006.01) | |
| C07D 213/81 | (2006.01) | |
| A61P 35/00 | (2006.01) | |

(52) U.S. Cl.
CPC ............ *C07D 401/12* (2013.01); *C07D 409/12* (2013.01); *C07D 413/12* (2013.01); *C07D 213/81* (2013.01)
USPC ........ 514/235.8; 544/365; 544/121; 544/364; 514/253.1; 514/253.13; 514/253.09

(58) Field of Classification Search
USPC .................. 514/235.8, 253.1, 253.13, 253.09; 544/365, 121, 364
See application file for complete search history.

(56) References Cited

FOREIGN PATENT DOCUMENTS

| | | |
|---|---|---|
| WO | WO2007123939 A2 | 11/2007 |
| WO | WO2008024963 A1 | 2/2008 |
| WO | WO2008024978 A2 | 2/2008 |
| WO | WO2008130879 A2 | 10/2008 |

OTHER PUBLICATIONS

Bai R.Y., et al., "Nucleophosmin-Anaplastic Lymphoma Kinase Associated with Anaplastic Large-Cell Lymphoma Activates the Phosphatidylinositol 3-Kinase/Akt Antiapoptotic Signaling Pathway," Blood, 2000, vol. 96 (13), pp. 4319-4327.
Bai R.Y., et al., "Nucleophosmin-Anaplastic Lymphoma Kinase of Large-Cell Anaplastic Lymphoma is a Constitutively Active Tyrosine Kinase that Utilizes Phospholipase C-Gamma to Mediate Its Mitogenicity," Molecular and Cellular Biology, 1998, vol. 18 (12), pp. 6951-6961.
Bischof D., et al., "Role of the Nucleophosmin (Npm) Portion of the Non-Hodgkin's Lymphoma-Associated Npm-Anaplastic Lymphoma Kinase Fusion Protein in Oncogenesis," Molecular and Cellular Biology, 1997, vol. 17 (4), pp. 2312-2325.
Chen Y., et al., "Oncogenic Mutations of Alk Kinase in Neuroblastoma," Nature, 2000, vol. 455 (7215), pp. 971-974.
Chiarle R., et al., "NPM-ALK Transgenic Mice Spontaneously Develop T-cell Lymphomas and Plasma Cell Tumors," Blood, 2003, vol. 101 (5), pp. 1919-1927.
Chiarle R., et al., "Stat3 is Required for ALK-mediated Lymphomagenesis and Provides a Possible Therapeutic Target," Nature Medicine, 2005, vol. 11 (6), pp. 623-629.
Chiarle R., et al., "The Anaplastic Lymphoma Kinase in the Pathogenesis of Cancer," Nature Reviews Cancer, 2008, vol. 8 (1), pp. 11-23.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.
Duyster J., et al., "Translocations Involving Anaplastic Lymphoma Kinase (ALK)," Oncogene, 2001, vol. 20 (40), pp. 5623-5637.
Fischer P., et al., "A Ki-1 (CD30)-positive Human Cell Line (Karpas 299) Established from a High-grade Non-Hodgkin's lymphoma, Showing a 2;5 Translocation and Rearrangement of the T-cell Receptor Beta-chain Gene," Blood, 1988, vol. 72 (1), pp. 234-240.
Fujimoto J., et al., "Characterization of the Transforming activity of p80, a Hyperphosphorylated Protein in a Ki-1 lymphoma Cell line with Chromosomal Translocation t(2;5)," Proceedings of the National Academy of Sciences, 1996, vol. 93 (9), pp. 4181-4186.

(Continued)

*Primary Examiner* — Kendra D Carter
*Assistant Examiner* — Jason A Deck
(74) *Attorney, Agent, or Firm* — Changxia Sun

(57) ABSTRACT

The present invention relates to compounds of formula (I) or pharmaceutical acceptable salts,

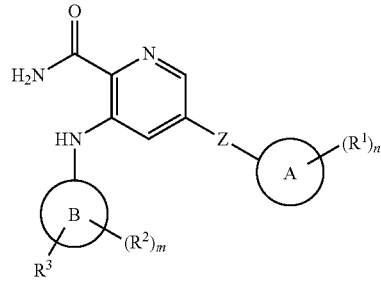

Formula (I)

wherein $R^1$, $R^2$, $R^3$, A, B, Z, n, and m are defined in the description. The present invention relates also to compositions containing said compounds which are useful for inhibiting kinases such as ALK and methods of treating diseases such as cancer.

15 Claims, No Drawings

(56) References Cited

OTHER PUBLICATIONS

George R.E., et al., "Activating Mutations in ALK Provide a Therapeutic Target in Neuroblastoma," Nature, 2008, vol. 455 (7215), pp. 975-978.

International Search Report and Written Opinion for Application No. PCT/US2012/021985, mailed on Feb. 29, 2012, 16 pages.

Janoueix-Lerosey I., et al., "Somatic and Germline Activating Mutations of the ALK Kinase Receptor in Neuroblastoma," Nature, 2008, vol. 455 (7215), pp. 967-970.

Kuefer M.U., et al., "Retrovirus-mediated Gene Transfer of NPM-ALK Causes Lymphoid Malignancy in Mice," Blood, 1997, vol. 90 (8), pp. 2901-2910.

Mosse Y.P., et al., "Identification of ALK as a Major Familial Neuroblastoma Predisposition Gene," Nature, 2008, vol. 455 (7215), pp. 930-935.

Pulford K., et al., "Anaplastic Lymphoma Kinase Proteins in Growth Control and Cancer," Journal of Cellular Physiology, 2004, vol. 199 (3), pp. 330-358.

Rodig S.J., et al., "Unique Clinicopathologic Features Characterize ALK-rearranged Lung Adenocarcinoma in the Western Population," Clinical Cancer Research, 2009, vol. 15 (16), pp. 5216-5223.

Shaw A.T., et al., "Clinical Features and Outcome of Patients with Non-small-cell Lung Cancer who Harbor EML4-ALK," Journal of Clinical Oncology, 2009, vol. 27 (26), pp. 4247-4253.

Soda M., et al., "A Mouse Model for EML4-ALK-positive Lung Cancer," Proceedings of the National Academy of Sciences, 2008, vol. 105 (50), pp. 19893-19897.

Soda M., et al., "Identification of the Transforming EML4-ALK Fusion Gene in Non-small-cell Lung Cancer," Nature, 2007, vol. 448 (7153), pp. 561-566.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Wong D.W., et al., "The EML4-ALK Fusion Gene is Involved in Various Histologic Types of Lung Cancers from Nonsmokers with Wild-type EGFR and KRAS," Cancer, 2009, vol. 115 (8), pp. 1723-1733.

PICOLINAMIDE INHIBITORS OF KINASES

CROSS-REFERENCE TO RELATED APPLICATIONS

This application claims priority to U.S. Provisional Application Ser. No. 61/434,998 filed Jan. 21, 2011, which is incorporated by reference in its entirety.

FIELD OF THE INVENTION

This invention pertains to compounds which inhibit the activity of anaphastic lymphoma kinase (ALK), methods of making the compounds, compositions containing the compounds, and methods of treatment using the compounds.

BACKGROUND OF THE INVENTION

Signaling through receptor tyrosine kinases (RTKs) regulates and fine-tunes many processes including cell growth, proliferation, differentiation, and apoptosis. The improper activation of RTKs is involved in the pathogenesis, growth, and metastasis of many cancers. The receptor tyrosine kinase ALK (Anaplastic Lymphoma Kinase) is a member of the insulin receptor superfamily that was initially identified from the t(2;5)(p23;q35) translocation in anaplastic large cell lymphoma (ALCL) (Fischer, P., et al. Blood, 72: 234-240. (1988)). The protein product of this translocation is ALK fused to nucleophosmin (NPM) (Morris et al., 1994). When fused to ALK, the dimerization domain of NPM results in constitutive dimerization and activation of ALK (reviewed in Chiarle, R., Nature reviews, 8:11-23 (2008)). Once activated, ALK recruits several adaptor proteins and stimulates multiple signaling pathways known to mediate tumor cell growth and survival including STAT3, PLC-γ, RAS-ERK1,2, and PI3K-AKT (Bai, R. Y., et al. Molecular and cellular biology 18: 6951-6961 (1998); Bai, R. Y., et al. Blood 96:4319-4327 (2000); Chiarle, R., et al. Nature medicine 11:623-629 (2005); Pulford, K., et al. Journal of cellular physiology 199: 330-358 (2004)). The dysregulation of ALK is highly oncogenic, as it is sufficient to induce cell transformation in a several immortalized cell lines (Bischof, D., et al. Molecular and cellular biology 17:2312-2325 (1997); Fujimoto, J., et al. Proceedings of the National Academy of Sciences of the United States of America 93: 4181-4186 (1996)) and to form tumors in animal models (Chiarle, R., et al. Blood 101: 1919-1927 (2003); Kuefer, M. U., et al. Blood 90: 2901-2910 (1997)). Moreover, NPM-ALK drives tumor formation, proliferation and survival in ALCL (reviewed in (Duyster, J., et al. Oncogene 20: 5623-5637 (2001)).

More recently, ALK translocations have been detected in ~5% of non-small cell lung cancers (NSCLC). Similar to ALK translocations in ALCL, the fusion proteins in NSCLC display constitutive ALK activity and drive tumor growth and survival (Soda et al., Nature 448: 561-566 (2007); Soda et al., Proceedings of the National Academy of Sciences of the United States of America 105: 19893-19897 (2008)). NSCLC tumors harboring ALK translocations are mutually exclusive from K-Ras or EGFR aberrations and predominantly occur in younger patients that are non-smokers (Rodig et al., Clin Cancer Res 15: 5216-5223 (2009); Shaw et al., J Clin Oncol 27: 4247-4253 (2009); Wong et al., Cancer 115: 1723-1733 (2009)). In addition to chromosomal rearrangements, activating point mutations and amplifications have been reported in a subset of sporadic and familial neuroblastomas, further expanding the spectrum of tumors dependent on ALK activity (Chen et al., Nature 455: 971-974 (2008); George et al., Nature 455: 975-978 (2008); Janoueix-Lerosey et al., Nature 455: 967-970 (2008); Mosse et al., Nature 455: 930-935 (2008)). Neuroblastomas with ALK genetic aberrations also are dependent on ALK for proliferation and survival, and cells expressing ALK containing activating mutations form tumors in animal models.

Inhibitors of RTKs have the potential to cause lethality in cancerous cells that are reliant on deregulated RTK activity while sparing normal tissues. Thus, small molecule inhibitors of ALK would be beneficial for therapeutic intervention in ALCL, NSCLC, neuroblastoma, and other cancers that are dependent on ALK for growth and survival.

SUMMARY OF THE INVENTION

The present invention has numerous embodiments. One embodiment of this invention, therefore, pertains to compounds that have formula (I)

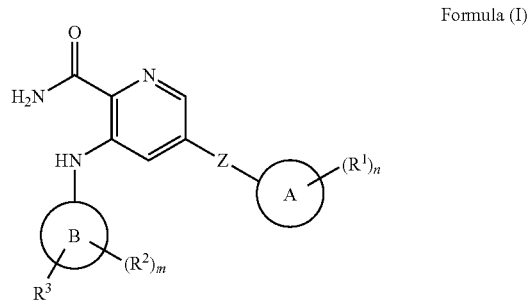

Formula (I)

wherein $R^1$, $R^2$, $R^3$, A, B, Z, m, and n are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Embodiments of Formula (I)

In one embodiment, the present invention is directed, in part, to a class of compounds having a structure of Formula I

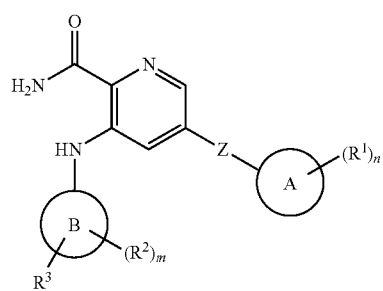

Formula (I)

wherein

A is phenyl, naphthyl, indenyl, $C_{3-8}$ cycloalkyl, 5-7 membered heterocycloalkyl, 5-7 membered heterocycloalkenyl, or 5-7 membered heteroaryl;

B is phenyl, pyridinyl, pyrimidinyl, pyrazinyl, pyridazinyl, or pyrazolinyl;

Z is bond, $C_{1-6}$ alkylene, $C_{2-6}$ alkenylene, —O—, or —N($R^4$)—;

$R^1$, at each occurrence, is independently selected from the group consisting of halo, CN, $NO_2$, $C_{1-6}$-alkyl, $C_{1-6}$-haloalkyl, aryl, $C_{3-8}$ cycloalkyl, heteroaryl, heterocycloalkyl, $OR^5$, $SR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$; wherein the $C_{3-8}$ cycloalkyl, aryl, heterocycloalkyl, and heteroaryl are optionally substituted with 1, 2, or 3 substituents independently selected from halo, $C_{1-4}$ alkyl, $C_{1-4}$ haloalkyl, CN, $NO_2$, $OR^a$, $SR^a$, $C(O)R^a$, $C(O)NR^bR^c$, $C(O)OR^a$, $OC(O)R^a$, $OC(O)NR^bR^c$, $NR^bR^c$, $NR^bC(O)R^a$, $S(O)R^a$, $S(O)NR^bR^c$, $S(O)_2R^a$, $NR^bS(O)_2R^a$, and $S(O)_2NR^bR^c$;

$R^2$, at each occurrence, is independently selected from the group consisting of halo, CN, OH, $C_{1-4}$ alkyl, $C_{1-4}$-haloalkyl, $C_{1-4}$ alkoxy, $C_{1-4}$ haloalkoxy, $C_{1-4}$-thioalkoxy, amino, $C_{1-4}$ alkylamino, and $C_{1-4}$ dialkylamino;

$R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, heterocycloalkyl-$C_{1-6}$-alkyl-, $OR^8$, $C(O)R^8$, $C(O)NR^9R^{10}$, $C(O)OR^8$, $OC(O)R^8$, $OC(O)NR^9R^{10}$, $NR^9R^{10}$, $NR^9C(O)R^8$, $S(O)R^8$, $S(O)NR^9R^{10}$, $S(O)_2R^8$, $NR^9S(O)_2R^8$, and $S(O)_2NR^9R^{10}$, wherein the $C_{3-8}$ cycloalkyl, aryl, heterocycloalkyl, and heteroaryl, alone or part of another moiety, are optionally substituted with one, two, or three $R^{11}$;

$R^4$ is H or $C_{1-6}$-alkyl;

$R^5$, $R^6$, and $R^7$, at each occurrence, are independently selected from H, $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^8$, $R^9$, and $R^{10}$, at each occurrence, are independently selected from H, $C_{1-6}$ alkyl, $C_{1-6}$ haloalkyl, heteroaryl-$C_{1-6}$-alkyl-, heterocycloalkyl-$C_{1-6}$-alkyl-, $R^{12}R^{13}N$—$C_{1-6}$-alkyl-, aryl, $C_{3-8}$ cycloalkyl, heteroaryl, and heterocycloalkyl, wherein the aryl, $C_{3-8}$ cycloalkyl, heteroaryl, and heterocycloalkyl, alone or as part of another moeity, is optionally substituted with halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, $C(O)C_{1-4}$ alkyl, $C(O)NH_2$, $C(O)NH(C_{1-4}$ alkyl), or $C(O)N(C_{1-4}$ alkyl)$_2$;

$R^{11}$ is selected from the group consisting of halo, $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, CN, $NO_2$, $OR^d$, $SR^d$, $C(O)R^d$, $C(O)NR^eR^f$, $C(O)OR^d$, $OC(O)R^d$, $OC(O)NR^eR^f$, $NR^eR^f$, $NR^eC(O)R^d$, $S(O)R^d$, $S(O)NR^eR^f$, $S(O)_2R^d$, $NR^eS(O)_2R^d$, and $S(O)_2NR^eR^f$, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl;

$R^{12}$ and $R^{13}$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^a$ is selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$ are independently selected from the group consisting of H, $C_{1-6}$ alkyl, $C_{1-6}$ haloalkyl, aryl, $C_{3-8}$ cycloalkyl, heteroaryl, heterocycloalkyl;

$R^d$ is selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$ are independently selected from the group consisting of H, $C_{1-6}$ alkyl, $C_{1-6}$ haloalkyl, aryl, $C_{3-8}$ cycloalkyl, heteroaryl, and heterocycloalkyl;

m is 0, 1, 2, or 3; and n is 0, 1, 2, or 3;

or a pharmaceutically acceptable salt or solvate thereof.

In one embodiment of formula (I), Z is $C_{1-6}$ alkylene. In another embodiment, Z is —$CH_2$—, —$CH_2CH_2$—, —$CH_2CH_2CH_2$—, or —$CH_2CH_2CH_2CH_2$—. In another embodiment, Z is —$CH(CH_3)$—, —$CH_2CH(CH_3)$—, —$CH(CH_3)CH_2$—, —$CH(CH_3)CH_2CH_2$—, —$CH_2CH(CH_3)CH_2$—, —$CH_2CH_2CH(CH_3)$—, —$C(CH_3)_2$—, —$CH_2C(CH_3)_2$—, —$C(CH_3)_2CH_2$—, —$CH_2CH_2C(CH_3)_2$—, —$CH_2C(CH_3)_2CH_2$—, or —$C(CH_3)_2CH_2CH_2$—. In another embodiment, Z is —$CH(CH_2CH_3)$—, —$CH_2CH(CH_2CH_3)$—, —$CH(CH_2CH_3)CH_2$—, —$CH(CH_2CH_3)CH_2CH_2$—, —$CH_2CH(CH_2CH_3)CH_2$—, —$CH_2CH_2CH(CH_2CH_3)$—, —$C(CH_2CH_3)_2$—, —$CH_2C(CH_2CH_3)_2$—, —$C(CH_2CH_3)_2CH_2$—, —$CH_2CH_2C(CH_2CH_3)_2$—, —$CH_2C(CH_2CH_3)_2CH_2$—, or —$C(CH_2CH_3)_2CH_2CH_2$—. In yet another embodiment, Z is —$CH_2$—, —$CH_2CH_2$—, —$CH(CH_3)$—, or —$C(CH_3)_2$—.

In another embodiment of formula (I), Z is $C_{2-6}$ alkenylene. In yet another embodiment of formula (I), Z is —CH═CH—, —$CH_2CH_2$═CH—, —CH═$CHCH_2$—, —$CH_2$—CH═CH—$CH_2$—, —CH═CH—$CH_2CH_2$—, or —$CH_2CH_2$—CH═CH—. In another embodiment of formula (I), Z is —CH(═$CH_2$)—, —$CH_2CH$(═$CH_2$)—, —CH(═$CH_2$)$CH_2$—, or —CH(═$CHCH_3$)—. In yet another embodiment of formula (I), Z is —CH═CH— or —CH(═$CH_2$)—.

In one embodiment of formula (I), Z is a bond.

In another embodiment of formula (I), Z is $NR^4$, wherein $R^4$ is H or $C_{1-6}$ alkyl.

In one embodiment of formula (I), A is phenyl, naphthyl, indenyl or $C_{3-8}$ cycloalkyl.

In yet another embodiment of formula (I), A is phenyl

In another embodiment of formula (I), A is a 5-7 membered heterocycloalkyl or heterocycloalkenyl. In another embodiment of formula (I), A is pyrrolidinyl, tetrahydrofuryl, tetrahydrothienyl, imidazolidinyl, pyrazolidinyl, piperidinyl, tetrahydropyranyl, piperazinyl, dioxanyl, morpholinyl, 2-oxopyrrolidinyl, 2,5-dioxopyrrolidinyl, 2-oxopiperidinyl, 4-oxopiperidinyl, or 2,6-dioxopiperidinyl. In yet another embodiment of formula (I), A is dihydrofuranyl, dihydrothiophenyl, pyrrolinyl, imidazolinyl, pyrazolinyl, thiazolinyl, isothiazolinyl, dihydropyranyl, oxathiazinyl, oxadiazinyl, or oxazinyl.

In one embodiment of formula (I), A is a 5-7 membered heteroaryl. In another embodiment, A is pyridyl, pyrazyl, pyridinyl, pyrimidinyl, pyridazinyl, 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl, or isothiazolyl.

A is optionally substituted with —$(R^1)_n$, wherein n is 0, 1, 2, or 3. In one embodiment, $R^1$ is selected from the group consisting of halo, CN, $NO_2$, $C_{1-6}$-alkyl, $C_{1-6}$-haloalkyl, aryl, $C_{3-8}$ cycloalkyl, heteroaryl, heterocycloalkyl, $OR^5$, $SR^5$, $C(O)R^5$, $C(O)NR^6R^7$, $C(O)OR^5$, $OC(O)R^5$, $OC(O)NR^6R^7$, $NR^6R^7$, $NR^6C(O)R^5$, $S(O)R^5$, $S(O)NR^6R^7$, $S(O)_2R^5$, $NR^6S(O)_2R^5$, and $S(O)_2NR^6R^7$; wherein the $C_{3-8}$ cycloalkyl, aryl, heterocycloalkyl, and heteroaryl are optionally substituted with 1, 2, or 3 substituents independently selected from halo, $C_{1-4}$ alkyl, $C_{1-4}$ haloalkyl, CN, $NO_2$, $OR^a$, $SR^a$, $C(O)R^a$, C(O)

NR$^b$R$^c$, C(O)OR$^a$, OC(O)R$^a$, OC(O)NR$^b$R$^c$, NR$^b$R$^c$, NR$^b$C(O)R$^a$, S(O)R$^a$, S(O)NR$^b$R$^c$, S(O)$_2$R$^a$, NR$^b$S(O)$_2$R$^a$, and S(O)$_2$NR$^b$R$^c$.

In another embodiment of formula (I), n is 0.

In another embodiment of formula (I), n is 1, 2, or 3, and R$^1$ is halo, OR$^5$, C$_{1-6}$ alkyl, C$_{1-6}$ haloalkyl, or CN, wherein R$^5$ is defined above. In another embodiment, n is 1 or 2, R$^1$ is OR$^5$, wherein R$^5$ is H or C$_{1-6}$ alkyl. In yet another embodiment of formula (I), n is 1, 2, or 3, and R$^1$ is halo.

In one embodiment of formula (I), n is 1 or 2, and R$^1$ is C(O)NR$^6$R$^7$, C(O)OR$^5$, NR$^6$C(O)R$^5$, NR$^6$S(O)$_2$R$^5$, or S(O)$_2$NR$^6$R$^7$, wherein R$^6$ and R$^7$ is defined above. In yet another embodiment, R$^1$ is NR$^6$S(O)$_2$R$^5$ or S(O)$_2$NR$^6$R$^7$, R$^6$ is hydrogen or C$_{1-6}$ alkyl, and R$^5$ and R$^7$ are independently C$_{1-6}$ alkyl, C$_{1-6}$ haloalkyl, aryl, C$_{3-8}$ cycloalkyl, heteroaryl, and heterocycloalkyl, wherein the aryl, C$_{3-8}$ cycloalkyl, heteroaryl, or heterocycloalkyl moiety is optionally substituted with C$_{1-4}$ alkyl.

In one embodiment of formula (I), B is phenyl, pyridinyl, pyrimidinyl, pyrazinyl, pyridazinyl, or pyrazolinyl. In another embodiment of formula (I), B is phenyl.

In one embodiment of formula (I), B is

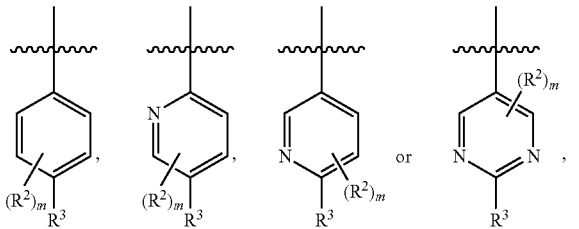

wherein R$^2$, R$^3$, and m are defined above. In another embodiment of formula (I), m is 0. In yet another embodiment of formula (I), m is 1 and R$^2$ is selected from the group consisting of halo, C$_{1-4}$ alkyl, and C$_{1-4}$ alkoxy. In another embodiment of formula (I), R$^3$ is selected from the group consisting of aryl, C$_{3-8}$ cycloalkyl, heteroaryl, heterocycloalkyl, aryl-C$_{1-6}$-alkyl-, C$_{3-8}$ cycloalkyl-C$_{1-6}$-alkyl-, heteroaryl-C$_{1-6}$-alkyl-, and heterocycloalkyl-C$_{1-6}$-alkyl-, wherein the C$_{3-8}$ cycloalkyl, aryl, heterocycloalkyl, and heteroaryl, alone or part of another moiety, are optionally substituted with one, two, or three R$^{11}$, wherein R$^{11}$ is defined above. In yet another embodiment of formula (I), R$^3$ is heterocycloalkyl, which is optionally substituted with one R$^{11}$, and R$^{11}$ is selected from the group consisting of C$_{1-4}$ alkyl, C$_{1-4}$ haloalkyl, amino-C$_{1-4}$-alkyl-, C$_{1-4}$ alkylamino-C$_{1-4}$ alkyl-, C$_{1-4}$ dialkylamino-C$_{1-4}$ alkyl-, hydroxy-C$_{1-4}$-alkyl-, C$_{1-4}$ alkyl-C$_{1-4}$ alkoxy, aryl, C$_{3-8}$ cycloalkyl, heteroaryl, heterocycloalkyl, aryl-(C$_{1-2}$ alkyl)-, C$_{3-8}$ cycloalkyl-(C$_{1-2}$ alkyl)-, heteroaryl-(C$_{1-2}$ alkyl)-, heterocycloalkyl-(C$_{1-2}$ alkyl)-, C(O)R$^d$, and S(O)$_2$R$^d$ wherein the aryl, C$_{3-8}$ cycloalkyl, heteroaryl, and heterocycloalkyl, alone or as part of another moiety, are optionally substituted with one, two or three substituents independently selected from halo and C$_{1-4}$ alkyl, and wherein R$^d$ is defined above.

In one embodiment of formula (I), B is

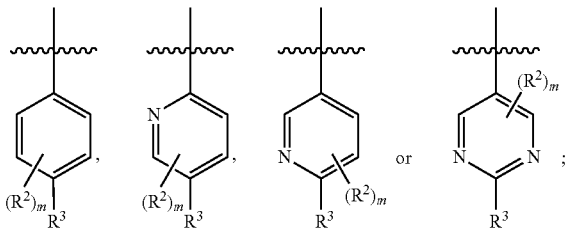

m is 0 or 1;

R$^2$ is halo, C$_{1-4}$ alkyl, or C$_{1-4}$ alkoxy;

R$^3$ is

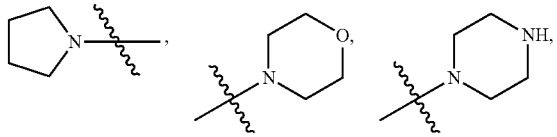

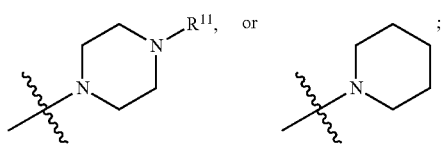

and

R$^{11}$ is C$_{1-4}$ alkyl, C$_{1-4}$ haloalkyl, amino-C$_{1-4}$-alkyl-, C$_{1-4}$ alkylamino-C$_{1-4}$ alkyl-, C$_{1-4}$ dialkylamino-C$_{1-4}$ alkyl-, and hydroxy-C$_{1-4}$-alkyl-, C$_{1-4}$ alkyl-C$_{1-4}$ alkoxy, aryl, cycloalkyl, heteroaryl, heterocycloalkyl, aryl-(C$_{1-2}$ alkyl)-, cycloalkyl-(C$_{1-2}$ alkyl)-, heteroaryl-(C$_{1-2}$ alkyl)-, or heterocycloalkyl-(C$_{1-2}$ alkyl)-, wherein the aryl, cycloalkyl, heteroaryl, and heterocycloalkyl, alone or as part of another moiety, are optionally substituted with 1, 2, or 3 substituents independently selected from halo and C$_{1-4}$ alkyl.

In another embodiment, B is

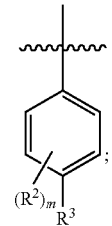

m is 0 or 1;

R$^2$ is halo, C$_{1-4}$ alkyl, or C$_{1-4}$ alkoxy;

R$^3$ is

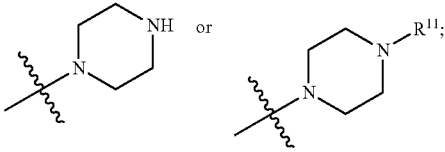

and R$^{11}$ is C$_{1-4}$ alkyl.

Embodiments of Formula (II)

In one embodiment, the present invention is directed, in part, to a class of compounds having a structure of Formula (II),

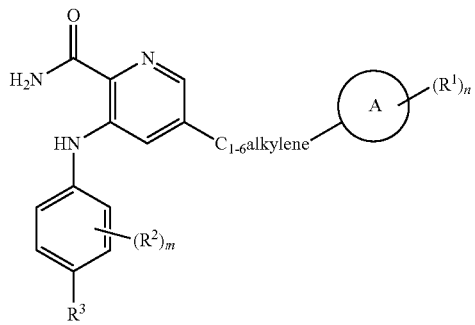

Formula (II)

wherein A, $R^1$, $R^2$, $R^3$, m, and n are as described in formula (I).

In one embodiment of formula (II), the $C_{1-6}$ alkylene is —$CH_2$—, —$CH_2CH_2$—, —$CH_2CH_2CH_2$—, or —$CH_2CH_2CH_2CH_2$—. In another embodiment, the $C_{1-6}$ alkylene is —$CH(CH_3)$—, —$CH_2CH(CH_3)$—, —$CH(CH_3)CH_2$—, —$CH(CH_3)CH_2CH_2$—, —$CH_2CH(CH_3)CH_2$—, —$CH_2CH_2CH(CH_3)$—, —$C(CH_3)_2$—, —$CH_2C(CH_3)_2$—, —$C(CH_3)_2CH_2$—, —$CH_2CH_2C(CH_3)_2$—, —$CH_2C(CH_3)_2CH_2$—, or —$C(CH_3)_2CH_2CH_2$—. In another embodiment, the $C_{1-6}$ alkylene is $CH(CH_2CH_3)$—, —$CH_2CH(CH_2CH_3)$—, —$CH(CH_2CH_3)CH_2$—, —$CH(CH_2CH_3)CH_2CH_2$—, —$CH_2CH(CH_2CH_3)CH_2$—, —$CH_2CH_2CH(CH_2CH_3)$—, —$C(CH_2CH_3)_2$—, —$CH_2C(CH_2CH_3)_2$—, —$C(CH_2CH_3)_2CH_2$—, —$CH_2CH_2C(CH_2CH_3)_2$—, —$CH_2C(CH_2CH_3)_2CH_2$—, or —$C(CH_2CH_3)_2CH_2CH_2$—. In yet another embodiment, the $C_{1-6}$ alkylene is —$CH_2$—, —$CH_2CH_2$—, —$CH(CH_3)$—, or —$C(CH_3)_2$—.

In one embodiment of formula (II), A is phenyl, naphthyl, or $C_{3-8}$ cycloalkyl. In another embodiment of formula (II), A is phenyl.

In one embodiment of formula (II), n is 0. In another embodiment of formula (II), n is 1, 2, or 3, and $R^1$ is halo, $OR^5$, $C_{1-6}$ alkyl, $C_{1-6}$ haloalkyl, or CN, wherein $R^5$ is described in formula (II). In another embodiment, n is 1 or 2, $R^1$ is $OR^5$, wherein $R^5$ is H or $C_{1-6}$ alkyl. In yet another embodiment of formula (II), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (II), m is 0. In yet another embodiment of formula (II), m is 1 and $R^2$ is selected from the group consisting of halo, $C_{1-4}$ alkyl, and $C_{1-4}$ alkoxy. In another embodiment of formula (II), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (II), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (II),
m is 0 or 1;
$R^2$ is halo, $C_{1-4}$ alkyl, or $C_{1-4}$ alkoxy;
$R^3$ is

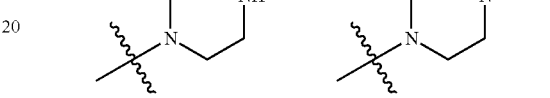

and $R^{11}$ is $C_{1-4}$ alkyl.

In one embodiment, the present invention is directed, in part, to a class of compounds having a structure of formula (IIa),

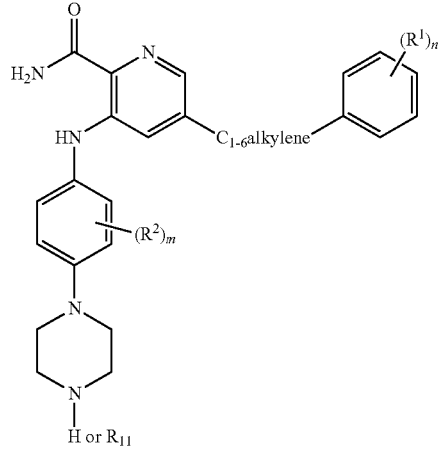

Formula (IIa)

wherein $R^1$, $R^2$, $R^{11}$, m and n are as described in formula (II).

In one embodiment of formula (IIa), the $C_{1-6}$ alkenylene is —$CH_2$—, —$CH_2CH_2$—, —$CH(CH_3)$—, or —$C(CH_3)_2$—.

In one embodiment of formula (IIa), n is 0. In another embodiment of formula (IIa), n is 1, 2, or 3, and $R^1$ is halo, $OR^5$, $C_{1-6}$ alkyl, $C_{1-6}$ haloalkyl, or CN, wherein $R^5$ is described in formula (IIa). In another embodiment, n is 1 or 2, $R^1$ is $OR^5$, wherein $R^5$ is H or $C_{1-6}$ alkyl. In yet another embodiment of formula (IIa), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^2$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (IIa), m is 0. In yet another embodiment of formula (II), m is 1 and $R^2$ is selected from the group consisting of halo, $C_{1-4}$ alkyl, and $C_{1-4}$ alkoxy.

In one embodiment of formula (IIa), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (IIa), $R^{11}$ is $C_{1-4}$ alkyl.

Embodiments of Formula (III)

In one embodiment, the present invention is directed, in part, to a class of compounds having a structure of Formula (III),

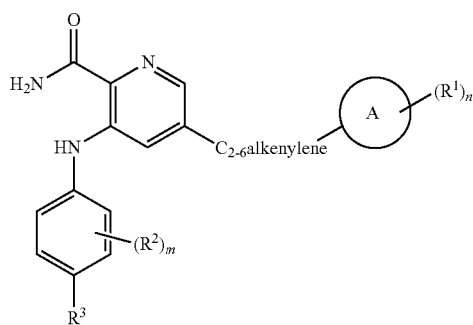

Formula (III)

wherein A, $R^1$, $R^2$, $R^3$, m, and n are as described in formula (I).

In one embodiment of formula (III), the $C_{1-6}$ alkylene is —CH=CH—, —CH$_2$CH$_2$=CH—, —CH=CHCH$_2$—, —CH$_2$—CH=CH—CH$_2$—, —CH=CH—CH$_2$CH$_2$—, or —CH$_2$CH$_2$—CH=CH—. In another embodiment of formula (III), Z is —CH(=CH$_2$)—, —CH$_2$CH(=CH$_2$)—, —CH(=CH$_2$)CH$_2$—, or —CH(=CHCH$_3$)—. In yet another embodiment of formula (III), Z is —CH=CH— or —CH(=CH$_2$)—.

In one embodiment of formula (III), A is phenyl.

In one embodiment of formula (III), n is 0. In another embodiment of formula (III), n is 1, 2, or 3, and $R^1$ is halo, $OR^5$, $C_{1-6}$ alkyl, $C_{1-6}$ haloalkyl, or CN, wherein $R^5$ is described in formula (III). In another embodiment, n is 1 or 2, $R^1$ is $OR^5$, wherein $R^5$ is H or $C_{1-6}$ alkyl. In yet another embodiment of formula (III), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^2$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (III), m is 0. In yet another embodiment of formula (III), m is 1 and $R^2$ is selected from the group consisting of halo, $C_{1-4}$ alkyl, and $C_{1-4}$ alkoxy. In another embodiment of formula (III), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (III), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (III),
m is 0 or 1;
$R^2$ is halo, $C_{1-4}$ alkyl, or $C_{1-4}$ alkoxy;
$R^3$ is

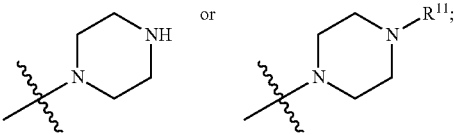

and $R^{11}$ is $C_{1-4}$ alkyl.

In one embodiment, the present invention is directed, in part, to a class of compounds having a structure of formula (IIIa),

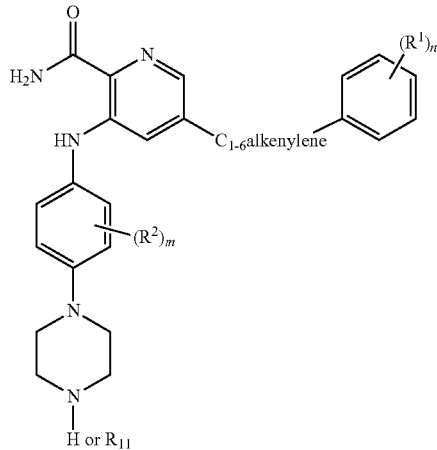

Formula (IIIa)

wherein $R^1$, $R^2$, $R^{11}$, m and n are as described in formula (III).

In one embodiment of formula (IIIa), the $C_{1-6}$ alkenylene is —CH=CH— or —CH(=CH$_2$)—.

In one embodiment of formula (IIIa), n is 0. In another embodiment of formula (IIIa), n is 1, 2, or 3, and $R^1$ is halo, $OR^5$, $C_{1-6}$ alkyl, $C_{1-6}$ haloalkyl, or CN, wherein $R^5$ is described in formula (IIIa). In another embodiment, n is 1 or 2, $R^1$ is $OR^5$, wherein $R^5$ is H or $C_{1-6}$ alkyl. In yet another embodiment of formula (IIIa), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^2$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, or heterocycloalkyl moiety is optionally substituted with $C_{1-4}$ alkyl.

In one embodiment of formula (IIIa), m is 0. In yet another embodiment of formula (II), m is 1 and $R^2$ is selected from the group consisting of halo, $C_{1-4}$ alkyl, and $C_{1-4}$ alkoxy.

In one embodiment of formula (IIIa), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (IIIa), $R^{11}$ is $C_{1-4}$ alkyl.

Embodiments of Formula (IV)

In one embodiment, the present invention is directed, in part, to a class of compounds having a structure of Formula (IV),

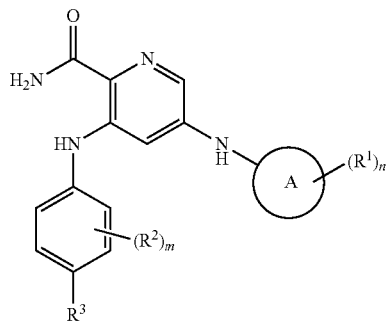

Formula (IV)

wherein A, $R^1$, $R^2$, $R^3$, m, and n are as described in formula (I).

In one embodiment of formula (IV), A is phenyl.

In one embodiment of formula (IV), n is 0. In another embodiment of formula (IV), n is 1, 2, or 3, and $R^1$ is halo, $OR^5$, $C_{1-6}$ alkyl, $C_{1-6}$ haloalkyl, or CN, wherein $R^5$ is described in formula (IV). In another embodiment, n is 1 or 2, $R^1$ is $OR^5$, wherein $R^5$ is H or $C_{1-6}$ alkyl. In yet another embodiment of formula (IV), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, or heterocycloalkyl moiety is optionally substituted with $C_{1-4}$ alkyl.

In one embodiment of formula (IV), m is 0. In yet another embodiment of formula (IV), m is 1 and $R^2$ is selected from the group consisting of halo, $C_{1-4}$ alkyl, and $C_{1-4}$ alkoxy. In another embodiment of formula (IV), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In another embodiment of formula (IV), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (IV),
m is 0 or 1;
$R^2$ is halo, $C_{1-4}$ alkyl, or $C_{1-4}$ alkoxy;
$R^3$ is

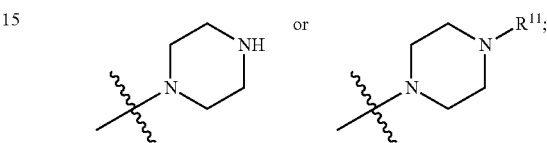

and $R^{11}$ is $C_{1-4}$ alkyl.

In one embodiment, the present invention is directed, in part, to a class of compounds having a structure of formula (IVa),

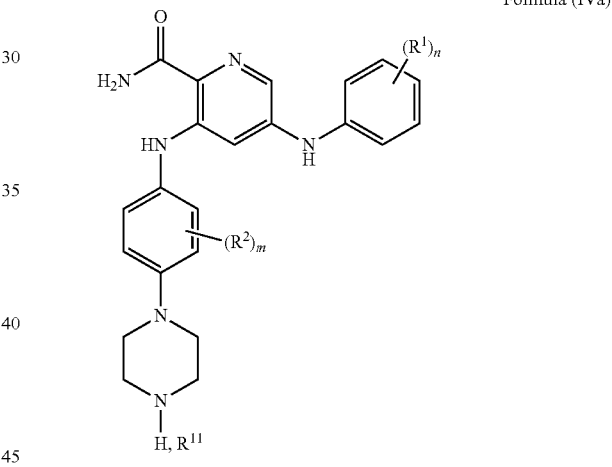

Formula (IVa)

wherein $R^1$, $R^2$, $R^{11}$, m and n are as described in formula (I) and/or formula (IV).

In one embodiment of formula (IVa), n is 0. In another embodiment of formula (IVa), n is 1, 2, or 3, and $R^1$ is halo, $OR^5$, $C_{1-6}$ alkyl, $C_{1-6}$ haloalkyl, or CN, wherein $R^5$ is described in formula (IVa). In another embodiment, n is 1 or 2, $R^1$ is $OR^5$, wherein $R^5$ is H or $C_{1-6}$ alkyl. In yet another embodiment of formula (IVa), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, or heterocycloalkyl moiety is optionally substituted with $C_{1-4}$ alkyl.

In one embodiment of formula (IVa), m is 0. In yet another embodiment of formula (IVa), m is 1 and $R^2$ is selected from the group consisting of halo, $C_{1-4}$ alkyl, and $C_{1-4}$ alkoxy.

In one embodiment of formula (IVa), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (IVa), $R^{11}$ is $C_{1-4}$ alkyl.

Embodiments of Formula (V)

In one embodiment, the present invention is directed, in part, to a class of compounds having a structure of Formula (V),

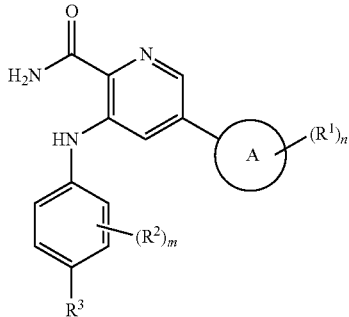

Formula (V)

wherein A, $R^1$, $R^2$, $R^3$, m, and n are as described in formula (I).

In one embodiment of formula (V), A is phenyl, pyridinyl, or pyrazyl. In another embodiment of formula (V), A is phenyl.

In one embodiment of formula (V), n is 0. In another embodiment of formula (V), n is 1, 2, or 3, and $R^1$ is halo, $OR^5$, $C_{1-6}$ alkyl, $C_{1-6}$ haloalkyl, or CN, wherein $R^5$ is described in formula (V). In another embodiment, n is 1 or 2, $R^1$ is $OR^5$, wherein $R^5$ is H or $C_{1-6}$ alkyl. In yet another embodiment of formula (V), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^2$ are independently $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with $C_{1-4}$ alkyl.

In one embodiment of formula (V), m is 0. In yet another embodiment of formula (V), m is 1 and $R^2$ is selected from the group consisting of halo, $C_{1-4}$ alkyl, and $C_{1-4}$ alkoxy. In another embodiment of formula (V), $R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, and heterocycloalkyl-$C_{1-6}$-alkyl-, wherein the $C_{3-8}$ cycloalkyl, aryl, heterocycloalkyl, and heteroaryl, alone or part of another moiety, are optionally substituted with one, two, or three $R^{11}$, wherein $R^{11}$ is defined above. In yet another embodiment of formula (V), $R^3$ heterocycloalkyl, which is optionally substituted with one $R^{11}$, and $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, heterocycloalkyl-($C_{1-2}$ alkyl)-, $C(O)R^d$, and $S(O)_2R^d$ wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl, and wherein $R^d$ is described in formula (I).

In another embodiment of formula (V), m is 0 or 1; $R^2$ is halo, $C_{1-4}$ alkyl, or $C_{1-4}$ alkoxy; $R^3$ is

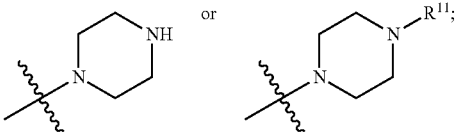

and $R^{11}$ is $C_{1-4}$ alkyl.

In one embodiment, the present invention is directed, in part, to a class of compounds having a structure of formula (Va),

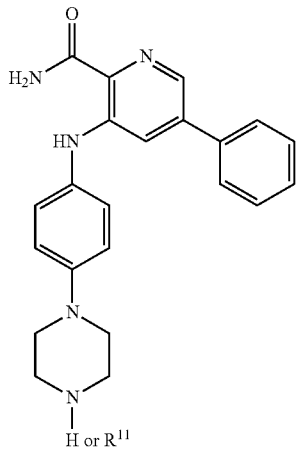

wherein $R^1$, $R^2$, $R^{11}$, m and n are as described in formula (V).

In one embodiment of formula (Va), n is 0. In another embodiment of formula (Va), n is 1, 2, or 3, and $R^1$ is halo, $OR^5$, $C_{1-6}$ alkyl, $C_{1-6}$ haloalkyl, or CN, wherein $R^5$ is described in formula (V). In another embodiment, n is 1 or 2, $R^1$ is $OR^5$, wherein $R^5$ is H or $C_{1-6}$ alkyl. In yet another embodiment of formula (Va), n is 1, 2, or 3, and $R^1$ is halo. In yet another embodiment, $R^1$ is $NR^6S(O)_2R^5$ or $S(O)_2NR^6R^7$, $R^6$ is hydrogen or $C_{1-6}$ alkyl, and $R^5$ and $R^7$ are independently $C_{1-6}$ alkyl, $C_{1-6}$ haloalkyl, aryl, $C_{3-8}$ cycloalkyl, heteroaryl, or heterocycloalkyl, wherein the aryl, $C_{3-8}$ cycloalkyl, heteroaryl, or heterocycloalkyl moiety is optionally substituted with $C_{1-4}$ alkyl.

In one embodiment of formula (Va), m is 0. In yet another embodiment of formula (Va), m is 1 and $R^2$ is selected from the group consisting of halo, $C_{1-4}$ alkyl, and $C_{1-4}$ alkoxy.

In one embodiment of formula (Va), $R^{11}$ is selected from the group consisting of $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$ alkoxy, $C_{3-8}$ cycloalkyl, heterocycloalkyl, aryl-($C_{1-2}$ alkyl)-, $C_{3-8}$ cycloalkyl-($C_{1-2}$ alkyl)-, heteroaryl-($C_{1-2}$ alkyl)-, and heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl. In one embodiment of formula (Va), $R^{11}$ is $C_{1-4}$ alkyl.

Specific embodiments contemplated as part of the invention include, but are not limited to, compounds of formula (I), for example:

5-(2,6-dichlorobenzyl)-3-{[2-methoxy-4-(piperazin-1-yl)phenyl]amino}pyridine-2-carboxamide;
5-[1-(2,6-dichlorophenyl)ethyl]-3-{[2-methoxy-4-(piperazin-1-yl)phenyl]amino}pyridine-2-carboxamide;
5-benzyl-3-{[4-(4-methylpiperazin-1-yl)phenyl]amino}pyridine-2-carboxamide;
5-benzyl-3-{[3-(4-methylpiperazin-1-yl)phenyl]amino}pyridine-2-carboxamide;
5-(cyclohexylmethyl)-3-{[4-(4-methylpiperazin-1-yl)phenyl]amino}pyridine-2-carboxamide;
3-{[4-(4-methylpiperazin-1-yl)phenyl]amino}-5-phenylpyridine-2-carboxamide;
5-benzyl-3-{[3-chloro-4-(4-methylpiperazin-1-yl)phenyl]amino}pyridine-2-carboxamide;
5-benzyl-3-{[3-methyl-4-(4-methylpiperazin-1-yl)phenyl]amino}pyridine-2-carboxamide;
5-benzyl-3-{[2-methyl-4-(4-methylpiperazin-1-yl)phenyl]amino}pyridine-2-carboxamide;
3-{[4-(4-methylpiperazin-1-yl)phenyl]amino}-5-(1-phenylvinyl)pyridine-2-carboxamide;
3-{[4-(4-methylpiperazin-1-yl)phenyl]amino}-5-(1-phenylethyl)pyridine-2-carboxamide;
5-(4-fluorobenzyl)-3-{[4-(4-methylpiperazin-1-yl)phenyl]amino}pyridine-2-carboxamide;
5-(2-fluorobenzyl)-3-{[4-(4-methylpiperazin-1-yl)phenyl]amino}pyridine-2-carboxamide;
5-(3-fluorobenzyl)-3-{[4-(4-methylpiperazin-1-yl)phenyl]amino}pyridine-2-carboxamide;
5-(2,6-difluorobenzyl)-3-{[4-(4-methylpiperazin-1-yl)phenyl]amino}pyridine-2-carboxamide;
5-(4-methoxybenzyl)-3-{[4-(4-methylpiperazin-1-yl)phenyl]amino}pyridine-2-carboxamide;
3-{[4-(4-methylpiperazin-1-yl)phenyl]amino}-5-(2-naphthylmethyl)pyridine-2-carboxamide;
5-(3,5-difluorobenzyl)-3-{[4-(4-methylpiperazin-1-yl)phenyl]amino}pyridine-2-carboxamide;
5-(3,4-difluorobenzyl)-3-{[4-(4-methylpiperazin-1-yl)phenyl]amino}pyridine-2-carboxamide;
5-(2,4-difluorobenzyl)-3-{[4-(4-methylpiperazin-1-yl)phenyl]amino}pyridine-2-carboxamide;
5-(2,5-difluorobenzyl)-3-{[4-(4-methylpiperazin-1-yl)phenyl]amino}pyridine-2-carboxamide;
5-(3-methoxybenzyl)-3-{[4-(4-methylpiperazin-1-yl)phenyl]amino}pyridine-2-carboxamide;
5-(2-chlorobenzyl)-3-{[4-(4-methylpiperazin-1-yl)phenyl]amino}pyridine-2-carboxamide;
5-(3-chlorobenzyl)-3-{[4-(4-methylpiperazin-1-yl)phenyl]amino}pyridine-2-carboxamide;
5-(4-chlorobenzyl)-3-{[4-(4-methylpiperazin-1-yl)phenyl]amino}pyridine-2-carboxamide;
5-(3-methylbenzyl)-3-{[4-(4-methylpiperazin-1-yl)phenyl]amino}pyridine-2-carboxamide;
5-(2-methylbenzyl)-3-{[4-(4-methylpiperazin-1-yl)phenyl]amino}pyridine-2-carboxamide;
5-(2-methoxybenzyl)-3-{[4-(4-methylpiperazin-1-yl)phenyl]amino}pyridine-2-carboxamide;
5-(4-methylbenzyl)-3-{[4-(4-methylpiperazin-1-yl)phenyl]amino}pyridine-2-carboxamide;
5-(2-chloro-6-fluorobenzyl)-3-{[4-(4-methylpiperazin-1-yl)phenyl]amino}pyridine-2-carboxamide;
5-(2,6-dichlorobenzyl)-3-{[4-(4-methylpiperazin-1-yl)phenyl]amino}pyridine-2-carboxamide;
5-(biphenyl-2-ylmethyl)-3-{[4-(4-methylpiperazin-1-yl)phenyl]amino}pyridine-2-carboxamide;
3-{[4-(4-methylpiperazin-1-yl)phenyl]amino}-5-[3-(trifluoromethyl)benzyl]pyridine-2-carboxamide;
5-[1-(3-fluorophenyl)ethyl]-3-{[4-(4-methylpiperazin-1-yl)phenyl]amino}pyridine-2-carboxamide;
5-[2-(3-fluorophenyl)propan-2-yl]-3-{[4-(4-methylpiperazin-1-yl)phenyl]amino}pyridine-2-carboxamide;
3-{[3-chloro-4-(4-methylpiperazin-1-yl)phenyl]amino}-5-[1-(3-fluorophenyl)ethyl]pyridine-2-carboxamide;
5-[1-(3-fluorophenyl)ethyl]-3-{[2-methoxy-4-(4-methylpiperazin-1-yl)phenyl]amino}pyridine-2-carboxamide;
5-(2,6-dichlorobenzyl)-3-{[2-methoxy-4-(4-methylpiperazin-1-yl)phenyl]amino}pyridine-2-carboxamide;
5-(2,6-dichlorobenzyl)-3-{[4-(piperazin-1-yl)phenyl]amino}pyridine-2-carboxamide;
5-(2-chloro-5-fluorobenzyl)-3-{[3-chloro-4-(4-methylpiperazin-1-yl)phenyl]amino}pyridine-2-carboxamide;
5-(2-chloro-5-fluorobenzyl)-3-{[2-methoxy-4-(piperazin-1-yl)phenyl]amino}pyridine-2-carboxamide;
5-(2-chloro-6-fluorobenzyl)-3-{[2-methoxy-4-(piperazin-1-yl)phenyl]amino}pyridine-2-carboxamide;
5-(2-chloro-6-fluorobenzyl)-3-[(2-methoxy-4-{4-[2-(morpholin-4-yl)ethyl]piperazin-1-yl}phenyl)amino]pyridine-2-carboxamide;
5-(2-chloro-6-fluorobenzyl)-3-[(4-{4-[2-(diethylamino)ethyl]piperazin-1-yl}-2-methoxyphenyl)amino]pyridine-2-carboxamide;
5-(2-chloro-6-fluorobenzyl)-3-({4-[4-(2-hydroxy-2-methylpropyl)piperazin-1-yl}-2-methoxyphenyl]amino)pyridine-2-carboxamide;
5-(2-chloro-6-fluorobenzyl)-3-{[2-methoxy-4-(4-methylpiperazin-1-yl)phenyl]amino}pyridine-2-carboxamide;
5-(2-chloro-6-fluorobenzyl)-3-{[4-(4-ethylpiperazin-1-yl)-2-methoxyphenyl]amino}pyridine-2-carboxamide;
5-(2-chloro-3,6-difluorobenzyl)-3-{[2-methoxy-4-(piperazin-1-yl)phenyl]amino}pyridine-2-carboxamide;
5-(2-methylphenyl)-3-{[4-(4-methylpiperazin-1-yl)phenyl]amino}pyridine-2-carboxamide;
5-(2-fluorophenyl)-3-{[4-(4-methylpiperazin-1-yl)phenyl]amino}pyridine-2-carboxamide;
5-(3-fluorophenyl)-3-{[4-(4-methylpiperazin-1-yl)phenyl]amino}pyridine-2-carboxamide;
5-(3-chlorophenyl)-3-{[4-(4-methylpiperazin-1-yl)phenyl]amino}pyridine-2-carboxamide;
5-(3-carbamoylphenyl)-3-{[4-(4-methylpiperazin-1-yl)phenyl]amino}pyridine-2-carboxamide;
3-{[4-(4-methylpiperazin-1-yl)phenyl]amino}-5-{3-[(methylsulfonyl)amino]phenyl}pyridine-2-carboxamide;
3-{[4-(4-methylpiperazin-1-yl)phenyl]amino}-5-{2-[(methylsulfonyl)amino]phenyl}pyridine-2-carboxamide;
3-{[4-(4-methylpiperazin-1-yl)phenyl]amino}-5-[(E)-2-phenylvinyl]pyridine-2-carboxamide;
3-{[2-methoxy-4-(4-methylpiperazin-1-yl)phenyl]amino}-5-{3-[(methylsulfonyl)amino]phenyl}pyridine-2-carboxamide;
5-(2-chlorophenyl)-3-{[4-(4-methylpiperazin-1-yl)phenyl]amino}pyridine-2-carboxamide;
5-(3-cyanophenyl)-3-{[4-(4-methylpiperazin-1-yl)phenyl]amino}pyridine-2-carboxamide;
5-{[4-(4-methylpiperazin-1-yl)phenyl]amino}-3,3'-bipyridine-6-carboxamide;
5-(2-cyanophenyl)-3-{[4-(4-methylpiperazin-1-yl)phenyl]amino}pyridine-2-carboxamide;
5-[3-(dimethylcarbamoyl)phenyl]-3-{[4-(4-methylpiperazin-1-yl)phenyl]amino}pyridine-2-carboxamide;
3-{[4-(4-methylpiperazin-1-yl)phenyl]amino}-5-(1H-pyrazol-4-yl)pyridine-2-carboxamide;

3-{[4-(4-methylpiperazin-1-yl)phenyl]amino}-5-(1-methyl-1H-pyrazol-4-yl)pyridine-2-carboxamide;

3-{[4-(4-methylpiperazin-1-yl)phenyl]amino}-5-(3-{[(2,2,2-trifluoroethyl)sulfonyl]amino}phenyl)pyridine-2-carboxamide;

5-{3-[(cyclopropylsulfonyl)amino]phenyl}-3-{[4-(4-methylpiperazin-1-yl)phenyl]amino}pyridine-2-carboxamide;

5-(3-{[(5-methyl-1,2-oxazol-4-yl)sulfonyl]amino}phenyl)-3-{[4-(4-methylpiperazin-1-yl)phenyl]amino}pyridine-2-carboxamide;

3-{[4-(4-methylpiperazin-1-yl)phenyl]amino}-5-{3-[(2-thienylsulfonyl)amino]phenyl}pyridine-2-carboxamide;

3-{[4-(4-methylpiperazin-1-yl)phenyl]amino}-5-(3-{[(1-methyl-1H-pyrazol-3-yl)sulfonyl]amino}phenyl)pyridine-2-carboxamide;

5-anilino-3-{[4-(4-methylpiperazin-1-yl)phenyl]amino}pyridine-2-carboxamide; and 5-{[2-(dimethylsulfamoyl)phenyl]amino}-3-{[4-(4-methylpiperazin-1-yl)phenyl]amino}pyridine-2-carboxamide.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

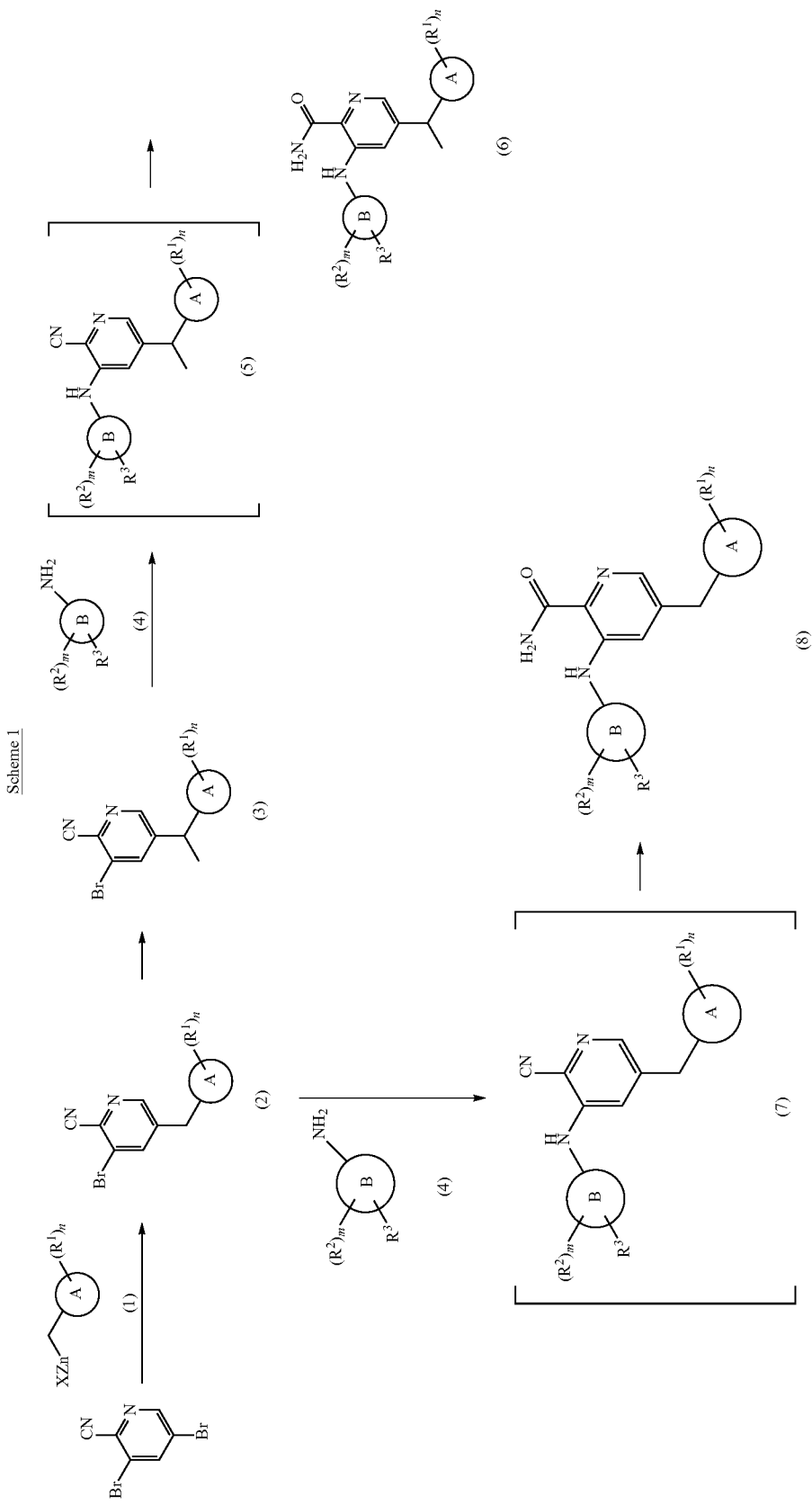

As shown in Scheme 1,3,5-dibromo-2-pyridinecarbonitrile can be reacted with a compound of formula (1), wherein X is chloride, bromine, iodine, or a triflate, and A, $R^1$, and n are as described herein, in the presence of a palladium or nickel catalyst to provide a compound of formula (2). Examples of ligands on the catalyst include but are not limited to triphenylphosphine, dppe, BINAP or chiraphos. The reaction is typically performed at elevated temperature in a solvent such as but not limited to tetrahydrofuran. Compounds of formula (2) can be treated at low temperature with a base such as but not limited to lithium bis(trimethylsilyl)amide, followed by the addition of methyl iodide, and then allowed to warm to room temperature, to provide compounds of formula (3). Compounds of formula (5) can be prepared by reacting compounds of formula (3) with compounds of formula (4) wherein B, $R^2$, and m are as described herein, a base, and a metal catalyst. Examples of bases, include, but are not limited to cesium carbonate, sodium bis(trimethylsilyl)amide, and sodium tert-butoxide. Examples of metal catalysts and ligands include palladium acetate and rac-BINAP (2,2'-bis(diphenylphosphino)-1,1'-binaphthyl), tris(dibenzylideneacetone)dipalladium(0) and rac-BINAP (2,2'-bis(diphenylphosphino)-1,1'-binaphthyl), and $PdCl_2(P(o\text{-tolyl})_3)_2$. Compounds of formula (5) can be treated with a base such as sodium t-butoxide in a solvent such as but not limited to t-butanol, to provide compounds of formula (6), which are representative of the compounds of this invention. The reaction is typically performed at an elevated temperature before neutralizing with aqueous hydrochloric acid.

Alternatively, compounds of formula (2) can be reacted with compounds of formula (4), wherein B, $R^2$, and m are as described herein, a base, and a metal catalyst. Examples of bases, include, but are not limited to cesium carbonate, sodium bis(trimethylsilyl)amide, and sodium tert-butoxide. Examples of metal catalysts and ligands include palladium acetate and rac-BINAP (2,2'-bis(diphenylphosphino)-1,1'-binaphthyl), tris(dibenzylideneacetone)dipalladium(0) and rac-BINAP (2,2'-bis(diphenylphosphino)-1,1'-binaphthyl), and $PdCl_2(P(o\text{-tolyl})_3)_2$. Compounds of formula (7) can be treated with a base such as sodium t-butoxide in a solvent such as but not limited to t-butanol, to provide compounds of formula (8), which are also representative of the compounds of this invention. The reaction is typically performed at an elevated temperature before neutralizing with aqueous hydrochloric acid.

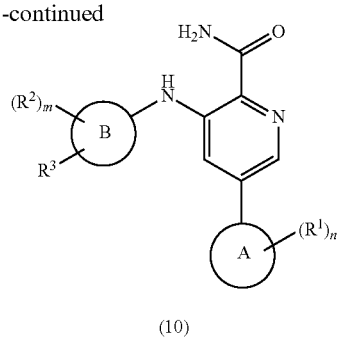

(10)

5-Bromo-3-fluoropicolinonitrile can be treated with compounds of formula (4), wherein B, $R^2$, and m are as described herein, in the presence of a base such as but not limited to triethylamine, followed by treatment with sodium t-butoxide as described in Scheme 1, to provide compounds of formula (9). The reaction is typically performed at elevated temperature in a microwave reactor in a solvent such as but not limited to t-butanol, followed by treatment with the sodium t-butoxide at elevated temperature. Compounds of formula (9) can be treated with boronic acids of formula (9A), wherein A, $R^1$, and n are as described herein, using Suzuki coupling conditions described herein, known to those skilled in the art, and readily available in the literature, to provide compounds of formula (10) which are representative of the compounds of this invention.

Scheme 3

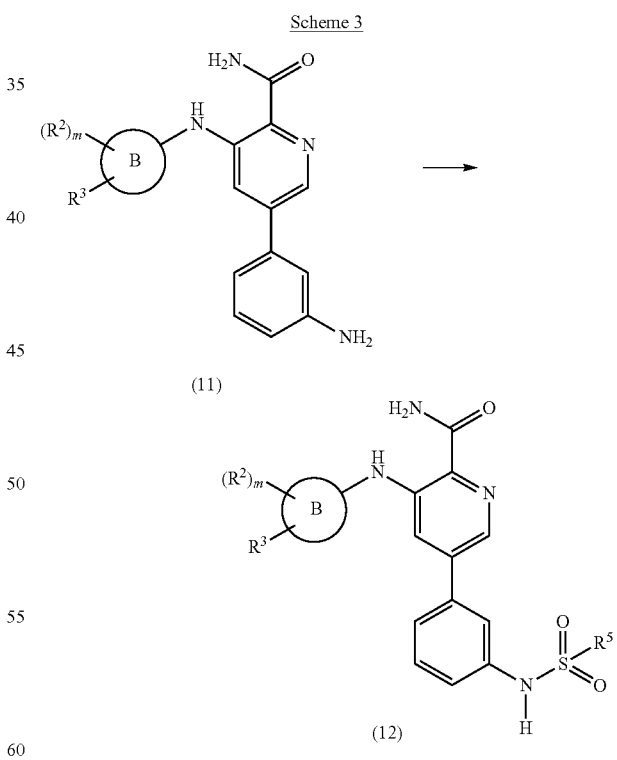

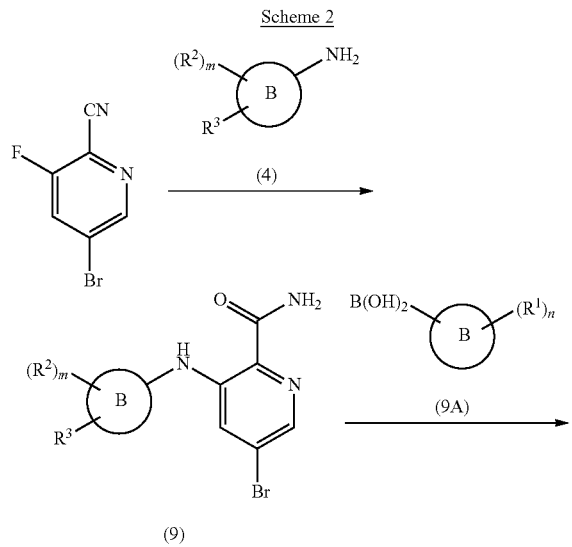

Compounds of formula (11), which can be prepared as described in Scheme 2, wherein the compound of formula (9A) is 3-aminophenyl boronic acid, can be reacted with a sulfonyl chloride of formula $R^5SO_2Cl$, to provide compounds of formula (12), which are representative of compounds of this invention.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-l) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT 103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, J. of Immunology 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (1) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTATAAE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECINT™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE®(acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

5-(2,6-dichlorobenzyl)-3-{[2-methoxy-4-(piperazin-1-yl)phenyl]amino}pyridine-2-carboxamide Example 1A 3,5-dibromo-2-pyridinecarbonitrile 3,5-Dibromopyridine (30.5 g, 0.12 mol) was dissolved in dichloromethane (80 mL) and methyltrioxorhenium (150 mg, 0.603 mmol) was added. Hydrogen peroxide (aqueous, 30%, 27 mL) was added slowly over 5 minutes, and the mixture was stirred at ambient temperature for 3 hours. An additional 40 mL of 30% hydrogen peroxide was added, and the reaction was stirred for 16 hours. Manganese dioxide (100 mg) was added, and the suspension was stirred for 40 minutes. The mixture was extracted with dichloromethane, dried (sodium sulfate), filtered and concentrated under reduced pressure. Ethyl acetate was added, and the suspension was refluxed for 30 minutes until solids dissolved, and then the mixture was allowed to cool to ambient temperature and left for 48 hours. 3,5-Dibromopyridine-1-oxide (28.05 g, 79%) was collected by vacuum filtration. MS (LC-MS) m/z 254 (M+H)$^+$. 3,5-Dibromopyridine-1-oxide (25.09 g, 0.099 mol) was then dissolved in acetonitrile (200 mL) and triethylamine (28 mL, 0.198 mol) and trimethylsilylcyanide (40 mL, 0.297 mol) were added. The reaction was stirred for 16 hours, diluted with dichloromethane, aqueous sodium carbonate, water, and then filtered through diatomaceous earth eluting with dichloromethane. The mixture was extracted with dichloromethane and the organics were washed with brine, dried (sodium sulfate), filtered and concentrated under reduced pressure. Purification by silica gel chromatography (30-70% ethyl acetate in hexanes) provided the title compound. MS (LC-MS) m/z 263 (M+H)$^+$.

Example 1B 3-bromo-5-(2,6-dichlorobenzyl)picolinonitrile

A solution of the product of EXAMPLE 1A (4.52 g, 15.34 mmol) in tetrahydrofuran (75 mL) was treated with palladium tetrakis(triphenylphosphine) (0.887 g, 0767 mmol) and 2,6-dichlorobenzyl zinc chloride (46 mL, 0.5M in tetrahydrofuran). The mixture was heated at 85° C. for 1 hour. After cooling to ambient temperature, the mixture was diluted with water and extracted with ethyl acetate. The organics were washed with brine, dried (sodium sulfate), filtered and concentrated under reduced pressure. Purification by silica gel chromatography (0-100% ethyl acetate in hexanes) provided the title compound. MS (LC-MS) m/z 342 (M+H)$^+$.

Example 1C tert-butyl 4-(4-(2-carbamoyl-5-(2,6-dichlorobenzyl) pyridin-3-ylamino)-3-methoxyphenyl)piperazine-1-carboxylate A dry flask was charged with EXAMPLE 1B (55.3 mg, 0.19 mmol), cesium carbonate (87 mg, 0.266 mmol), palladium acetate (2.1 mg, 0.0095 mmol), rac-BINAP (2,2'-bis (diphenylphosphino)-1,1'-binaphthyl) (8.9 mg, 0.0143 mmol), tert-butyl 4-(4-amino-3-methoxyphenyl)piperazine-1-carboxylate (28 mg, 0.228 mmol) and toluene (5 mL). The mixture was refluxed for 5 hours. The reaction mixture was concentrated under reduced pressure, and the residue was dissolved in t-butanol (2 mL) and treated with sodium t-butoxide (0.6 mmol). The reaction was stirred at 85° C. for 15 minutes, diluted with dichloromethane and neutralized to pH=6-7 with 1N aqueous HCl. It was filtered through diatomaceous earth eluting with dichloromethane and the filtrate was concentrated under reduced pressure. Purification by silica gel chromatography (0-10% methanol in dichloromethane) provided the title compound.

Example 1D 5-(2,6-dichlorobenzyl)-3-{[2-methoxy-4-(piperazin-1-yl)phenyl]amino}pyridine-2-carboxamide A solution of the product of EXAMPLE 1C (76 mg, 0.13 mmol) in dioxane (1 mL) was treated with 4N HCl in dioxane (1 mL) and stirred at ambient temperature for 3 hours. The reaction mixture was concentrated under reduced pressure; and the residue was neutralized with 1N aqueous NaOH and extracted with dichloromethane. The organics were washed with brine, dried (sodium sulfate), filtered and concentrated under reduced pressure. Purification by silica gel chromatography (0-10% methanol in dichloromethane) provided the title compound. $^1$H NMR (DMSO-d$_6$) δ ppm 2.85 (t, 4H, J=5.2 Hz), 3.05 (t, 4H, J=5.2 Hz), 3.66 (s, 3H), 4.19 (s, 2H), 6.39-6.42 (m, 1H), 6.57 (s, 1H), 6.88-6.97 (m, 2H), 7.33 (t, 1H, J=8.4 Hz), 7.48-7.51 (m, 3H), 7.73 (s, 1H), 8.06 (s, 1H), 9.88 (s, 1H); MS (ESI) m/z 487 (M+H)$^+$.

Example 2

5-[1-(2,6-dichlorophenyl)ethyl]-3-{[2-methoxy-4-(piperazin-1-yl)phenyl]amino}pyridine-2-carboxamide Example 2A 3-bromo-5-(1-(2,6-dichlorophenyl)ethyl)picolinonitrile EXAMPLE 1B (833 mg, 2.436 mmol) in dry tetrahydrofuran (20 mL) was cooled to −78° C. and treated with 1M lithium bis(trimethylsilyl)amide in tetrahydrofuran (3.04 mL, 3.04 mmol). The reaction was stirred at this temperature for 45 minutes, treated with CH$_3$I (0.198 mL, 3.17 mmol) and stirred slowly, warming to 0° C. over 3 hours. It was quenched with aqueous ammonium chloride solution and extracted with ethyl acetate. The combined organic layers were dried (sodium sulfate), filtered and concentrated. Purification by silica gel chromatography (0-30% ethyl acetate in hexanes) provided the title compound.

Example 2B tert-butyl 4-(4-(2-carbamoyl-5-(1-(2,6-dichlorophenyl)ethyl)pyridin-3-ylamino)-3-methoxyphenyl)piperazine-1-carboxylate EXAMPLE 2A (100 mg, 0.281 mmol) and tert-butyl 4-(4-amino-3-methoxyphenyl)piperazine-1-carboxylate (95 mg, 0.309 mmol) were processed using the method described in EXAMPLE 1C to afford the title compound.

Example 2C

5-[1-(2,6-dichlorophenyl)ethyl]-3-{[2-methoxy-4-(piperazin-1-yl)phenyl]amino}pyridine-2-carboxamide EXAMPLE 2B was processed using the method described in EXAMPLE 1D to afford the title compound. $^1$H NMR (DMSO-d$_6$) δ ppm 1.65 (d, 3H, J=7.2 Hz), 2.87 (t, 4H, J=5.2 Hz), 3.07 (t, 4H, J=5.2 Hz), 3.69 (s, 3H), 4.98 (q, 1H, J=7.2 Hz), 6.40 (dd, 1H, J=2.4 Hz, J=8.8 Hz), 6.59 (d, 1H, J=2.4 Hz), 6.94-6.99 (m, 2H), 7.37 (t, 3H, J=8.0 Hz), 7.46-7.50 (m, 3H), 7.63 (s, 1H), 8.05 (d, 1H, J=2.4 Hz), 9.90 (s, 1H); MS (ESI) m/z 501 (M+H)$^+$.

Example 3

5-benzyl-3-{[4-(4-methylpiperazin-1-yl)phenyl]amino}pyridine-2-carboxamide

Example 3A 5-benzyl-3-bromopicolinonitrile

EXAMPLE 1A and benzyl zinc bromide were processed using the method described in EXAMPLE 1B to afford the title compound.

Example 3B 5-benzyl-3-{[4-(4-methylpiperazin-1-yl)phenyl]amino}pyridine-2-carboxamide EXAMPLE 3A and 4-(4-methylpiperazin-1-yl)aniline were processed using the method described in EXAMPLE 1C to afford the title compound. $^1$H NMR (CDCl$_3$) δ ppm 2.37 (s, 3H), 2.61 (t, J=4.4, 5.2 Hz, 4H), 3.20 (t, J=4.8, 5.6 Hz, 4H), 3.85 (s, 2H), 6.91 (d, J=4.0 Hz, 2H), 7.08 (d, J=3.2 Hz, 2H), 7.12 (d, J=1.1 Hz, 2H), 7.22 (m, 2H), 7.25 (m, 1H), 7.29 (m, 2H), 7.71 (s, 1H), 7.90 (d, J=4.0 Hz, 1H), 9.88 (s, 1H); MS (ESI) m/z 402 (M+H)$^+$.

Example 4

5-benzyl-3-{[3-(4-methylpiperazin-1-yl)phenyl]amino}pyridine-2-carboxamide

EXAMPLE 3A and 3-(4-methylpiperazin-1-yl)aniline were processed using the method described in EXAMPLE 1C to afford the title compound. $^1$H NMR (DMSO-d$_6$) δ ppm 10.36 (s, 1H), 8.18-8.13 (m, 1H), 7.91 (d, J=1.7, 1H), 7.62-7.57 (m, 1H), 7.47 (d, J=1.7, 1H), 7.33-7.17 (m, 5H), 7.14 (t, J=8.0, 1H), 6.64 (dd, J=8.3, 2.3, 1H), 6.60 (d, J=2.2, 1H), 6.54 (dd, J=7.8, 1.9, 1H), 3.94 (s, 2H), 3.08-2.97 (m, 4H), 2.44-2.38 (m, 4H), 2.22 (s, 3H); MS (ESI) m/z 402 (M+H)$^+$.

Example 5

5-(cyclohexylmethyl)-3-{[4-(4-methylpiperazin-1-yl)phenyl]amino}pyridine-2-carboxamide

Example 5A 5-cyclohexylmethyl-3-bromopicolinonitrile

EXAMPLE 1A and cyclohexylmethyl zinc bromide were processed using the method described in EXAMPLE 1B to afford the title compound.

Example 5B 5-(cyclohexylmethyl)-3-{[4-(4-methylpiperazin-1-yl)phenyl]amino}pyridine-2-carboxamide EXAMPLE 5A and 4-(4-methylpiperazin-1-yl)aniline were processed using the method described in EXAMPLE 1C and purified by RP HPLC (0.1% TFA/acetonitrile) to afford the title compound as the trifluoroacetate salt. $^1$H NMR (DMSO-d$_6$) δ ppm 10.23 (s, 1H), 8.13 (s, 1H), 7.75 (s, 1H), 7.54 (s, 1H), 7.21-7.01 (m, 5H), 3.99-3.65 (m, 6H), 3.58-3.49 (m, 5H), 2.88 (d, J=3.7, 1H), 1.68-1.54 (m, 4H), 1.49-1.39 (m, 1H), 1.35-1.09 (m, 3H), 0.96-0.81 (m, 2H); MS (ESI) m/z 408 (M+H)$^+$.

Example 6

3-{[4-(4-methylpiperazin-1-yl)phenyl]amino}-5-phenylpyridine-2-carboxamide

Example 6A 3-bromo-5-phenylpicolinonitrile

EXAMPLE 1A and phenyl zinc bromide were processed using the method described in EXAMPLE 1B to afford the title compound.

Example 6B

3-{[4-(4-methylpiperazin-1-yl)phenyl]amino}-5-phenylpyridine-2-carboxamide

EXAMPLE 6A and 4-(4-methylpiperazin-1-yl)aniline were processed using the method described in EXAMPLE 1C and purified by RP HPLC (0.1% TFA/acetonitrile) to afford the title compound as the trifluoroacetate salt. $^1$H NMR (DMSO-d$_6$) δ ppm 10.34 (s, 1H), 8.26-8.19 (s, 1H), 7.69-7.60 (m, 2H), 7.56 (d, J=2.0, 1H), 7.53-7.40 (m, 3H), 7.24 (s, 2H), 7.12-7.02 (m, 2H), 3.08-2.97 (m, 4H), 2.44-2.38 (m, 4H), 2.22 (s, 3H); MS (ESI) m/z 388 (M+H)$^+$.

Example 7

5-benzyl-3-{[3-chloro-4-(4-methylpiperazin-1-yl)phenyl]amino}pyridine-2-carboxamide EXAMPLE 3A and 3-chloro-4-(4-methylpiperazin-1-yl)aniline were processed using the method described in EXAMPLE 1C and purified by RP HPLC (0.1% TFA/acetonitrile) to afford the title compound as the trifluoroacetate salt. $^1$H NMR (DMSO-d$_6$) δ ppm 12.45 (s, 1H), 10.44 (s, 1H), 8.19 (bs, 1H), 7.94 (d, J=1.7, 1H), 7.67-7.62 (bs, 1H), 7.45 (d, J=1.8, 1H), 7.35-7.08 (m, 7H), 3.97 (s, 2H), 3.92-3.89 (m, 2H), 3.80-3.72 (m, 2H), 3.59 (s, 3H), 2.54-2.47 (m, 4H); MS (ESI) m/z 436 (M+H)$^+$.

Example 8

5-benzyl-3-{[3-methyl-4-(4-methylpiperazin-1-yl)phenyl]amino}pyridine-2-carboxamide EXAMPLE 3A and 3-methyl-4-(4-methylpiperazin-1-yl)aniline were processed using the method described in EXAMPLE 1C and purified by RP HPLC (0.1% TFA/acetonitrile) to afford the title compound as the trifluoroacetate salt. $^1$H NMR (DMSO-d$_6$) δ ppm 12.40 (s, 1H), 10.06 (d, J=5.4, 1H), 8.11 (s, 1H), 7.80 (d, J=1.6, 1H), 7.54 (s, 1H), 7.28 (t, J=7.3, 2H), 7.23-7.10 (m, 4H), 7.03-6.97 (m, 1H), 6.97-6.90 (m, 1H), 3.96 (s, 2H), 3.88-3.82 (m, 2H), 3.78-3.72 (m, 4H), 3.56 (s, 3H), 3.29 (t, J=11.1, 2H), 2.10 (s, 3H); MS (ESI) m/z 416 (M+H)$^+$.

Example 9

5-benzyl-3-{[2-methyl-4-(4-methylpiperazin-1-yl)phenyl]amino}pyridine-2-carboxamide EXAMPLE 3A and 2-methyl-4-(4-methylpiperazin-1-yl)aniline were processed using the method described in EXAMPLE 1C and purified by RP HPLC (0.1% TFA/acetonitrile) to afford the title compound as the trifluoroacetate salt. $^1$H NMR (DMSO-d$_6$) δ ppm 12.33 (s, 1H), 10.06 (d, J=5.3, 1H), 8.11 (s, 1H), 7.80 (d, J=1.6, 1H), 7.54 (s, 1H), 7.28 (t, J=7.4, 2H), 7.22-7.04 (m, 4H), 7.03-6.81 (m, 2H), 3.88 (s, 2H), 3.86-3.82 (m, 2H), 3.78-3.72 (m, 4H), 3.56 (s, 3H), 3.33-3.25 (t, J=11.1, 2 H), 2.10 (s, 3H); MS (ESI) m/z 416 (M+H)$^+$.

Example 10

3-{[4-(4-methylpiperazin-1-yl)phenyl]amino}-5-(1-phenylvinyl)pyridine-2-carboxamide Example 10A 3-bromo-5-(1-phenyl-vinyl)picolinonitrile EXAMPLE 1A and 1-phenylvinyl zinc bromide were processed using the method described in EXAMPLE 1B to afford the title compound.

Example 10B

3-{[4-(4-methylpiperazin-1-yl)phenyl]amino}-5-(1-phenylvinyl)pyridine-2-carboxamide EXAMPLE 10A and 4-(4-methylpiperazin-1-yl)aniline were processed using the method described in EXAMPLE 1C to afford the title compound. $^1$H NMR (CDCl$_3$) δ ppm 2.35 (s, 3H), 2.58 (t, J=4.8, 5.2 Hz, 4H), 3.17 (t, J=4.8, 5.2 Hz, 4H), 5.44 (s, 1H), 5.55 (s, 1H), 6.88 (d, J=11 Hz, 2H), 7.10 (d, J=8.8 Hz, 2H), 7.32 (m, 6H), 7.37 (s, 1H), 7.79 (s, 1H), 7.94 (d, J=3.6 Hz, 1H), 9.94 (s, 1H); MS (LC-MS) m/z 414 (M+H)$^+$.

Example 11

3-{[4-(4-methylpiperazin-1-yl)phenyl]amino}-5-(1-phenylethyl)pyridine-2-carboxamide Example 11A 3-bromo-5-(1-phenyl-ethyl)picolinonitrile EXAMPLE 1A and 1-phenylethyl zinc bromide were processed using the method described in EXAMPLE 1B to afford the title compound.

Example 11B

3-{[4-(4-methylpiperazin-1-yl)phenyl]amino}-5-(1-phenylethyl)pyridine-2-carboxamide EXAMPLE 11A and 4-(4-methylpiperazin-1-yl)aniline were processed using the method described in EXAMPLE 1C to afford the title compound. $^1$H NMR (CDCl$_3$) δ ppm 1.57 (d, J=9.0 Hz, 3H), 2.38 (s, 3H), 2.62 (t, J=5.6, 4.0 Hz, 4H), 3.21 (t, J=5.6, 4.0 Hz, 4H), 4.04 (m, J=7.2 Hz, 1H), 5.32 (s, 1H), 6.91 (d, J=8.0 Hz, 2H), 7.08 (d, J=8.0 Hz, 2H), 7.17 (d, J=8.0 Hz, 2H), 7.20 (m, 1H), 7.29 (m, 2H), 7.72 (d, J=2.0 Hz, 1H), 7.88 (d, J=4.0 Hz, 1H), 9.89 (s, 1H); MS (LC-MS) m/z 416 (M+H)$^+$.

Example 12

5-(4-fluorobenzyl)-3-{[4-(4-methylpiperazin-1-yl)phenyl]amino}pyridine-2-carboxamide Example 12A 3-bromo-5-(4-fluorobenzyl)picolinonitrile EXAMPLE 1A and 4-fluorobenzyl zinc bromide were processed using the method described in EXAMPLE 1B to afford the title compound.

Example 12B 5-(4-fluorobenzyl)-3-{[4-(4-methylpiperazin-1-yl)phenyl]amino}pyridine-2-carboxamide EXAMPLE 12A and 4-(4-methylpiperazin-1-yl)aniline were processed using the method described in EXAMPLE 1C to afford the title compound. $^1$H NMR (CDCl$_3$) δ ppm 2.30 (s, 3H), 2.53 (t, J=4.8, 5.2 Hz, 4H), 3.13 (t, J=5.2 Hz, 4H), 3.75 (s, 2H), 5.29 (s, 1H), 6.84 (d, J=4.4 Hz, 2H), 6.89 (m, J=4.4 Hz, 2H), 7.01 (d, J=8.8 Hz, 2H), 7.02 (m, 2H), 7.10 (d, J=2.0 Hz, 1H), 7.60 (d, J=2.0 Hz, 1H), 7.81 (d, J=4.0 Hz, 1H), 9.81 (s, 1H); MS (LC-MS) m/z 420 (M+H)$^+$.

Example 13

5-(2-fluorobenzyl)-3-{[4-(4-methylpiperazin-1-yl)phenyl]amino}pyridine-2-carboxamide Example 13A 3-bromo-5-(2-fluorobenzyl)picolinonitrile EXAMPLE 1A and 2-fluorobenzyl zinc bromide were processed using the method described in EXAMPLE 1B to afford the title compound.

Example 13B 5-(2-fluorobenzyl)-3-{[4-(4-methylpiperazin-1-yl)phenyl]amino}pyridine-2-carboxamide EXAMPLE 13A and 4-(4-methylpiperazin-1-yl)aniline were processed using the method described in EXAMPLE 1C to afford the title compound. $^1$H NMR (CDCl$_3$) δ ppm 2.37 (s, 3H), 2.61 (t, J=6.0, 6.5 Hz, 4H), 3.13 (t, J=4.8 Hz, 4H), 3.77 (s, 2H), 5.38 (s, 1H), 6.84 (d, J=2.4 Hz, 2H), 6.97 (m, 3H), 7.02 (d, J=2.4 Hz, 2H), 7.13 (m, 1H), 7.19 (s, 1H), 7.72 (d, J=2.0 Hz, 1H), 7.89 (d, J=4.0 Hz, 1H), 9.89 (s, 1H); MS (LC-MS) m/z 420 (M+H)$^+$.

Example 14

5-(3-fluorobenzyl)-3-{[4-(4-methylpiperazin-1-yl)phenyl]amino}pyridine-2-carboxamide

Example 14A 3-bromo-5-(3-fluorobenzyl)picolinonitrile

EXAMPLE 1A and 3-fluorobenzyl zinc bromide were processed using the method described in EXAMPLE 1B to afford the title compound.

Example 14B 5-(3-fluorobenzyl)-3-{[4-(4-methylpiperazin-1-yl)phenyl]amino}pyridine-2-carboxamide EXAMPLE 14A and 4-(4-methylpiperazin-1-yl)aniline were processed using the method described in EXAMPLE 1C to afford the title compound. $^1$H NMR (CDCl$_3$) δ ppm 2.29 (s, 3H), 2.53 (t, J=4.8 Hz, 4H), 3.21 (t, J=4.8, 5.2 Hz, 4H), 3.87 (s, 2H), 5.38 (s, 1H), 6.74 (d, J=9.6 Hz, 1H), 6.83 (m, J=8.8 Hz, 4H), 7.02 (d, J=8.8 Hz, 2H), 7.15 (m, 2H), 7.61 (d, J=1.5 Hz, 1H), 7.82 (d, J=4.0 Hz, 1H), 9.82 (s, 1H); MS (LC-MS) m/z 420 (M+H)$^+$.

Example 15

5-(2,6-difluorobenzyl)-3-{[4-(4-methylpiperazin-1-yl)phenyl]amino}pyridine-2-carboxamide

Example 15A 3-bromo-5-(2,6-difluorobenzyl)picolinonitrile

EXAMPLE 1A and 2,6-difluorobenzyl zinc bromide were processed using the method described in EXAMPLE 1B to afford the title compound.

Example 15B 5-(2,6-difluorobenzyl)-3-{[4-(4-methylpiperazin-1-yl)phenyl]amino}pyridine-2-carboxamide EXAMPLE 15A and 4-(4-methylpiperazin-1-yl)aniline were processed using the method described in EXAMPLE 1C to afford the title compound. $^1$H NMR (CDCl$_3$) δ ppm 2.31 (s, 3H), 2.55 (t, J=4.4, 5.2 Hz, 4H), 3.15 (t, J=4.4, 5.2 Hz, 4H), 3.81 (s, 2H), 5.27 (s, 1H), 6.80 (t, J=7.6, 8 Hz, 2H), 6.86 (d, J=12 Hz, 2H), 7.02 (d, J=12 Hz, 2H), 7.11 (m, 1H), 7.26 (s, 1H), 7.68 (s, 1H), 7.81 (d, J=4.0 Hz, 1H), 9.82 (s, 1H); MS (LC-MS) m/z 438 (M+H)$^+$.

Example 16

5-(4-methoxybenzyl)-3-{[4-(4-methylpiperazin-1-yl)phenyl]amino}pyridine-2-carboxamide

Example 16A 3-bromo-5-(4-methoxybenzyl)picolinonitrile

EXAMPLE 1A and 4-methoxybenzyl zinc bromide were processed using the method described in EXAMPLE 1B to afford the title compound.

Example 16B 5-(4-methoxybenzyl)-3-{[4-(4-methylpiperazin-1-yl)phenyl]amino}pyridine-2-carboxamide EXAMPLE 16A and 4-(4-methylpiperazin-1-yl)aniline were processed using the method described in EXAMPLE 1C to afford the title compound. $^1$H NMR (CDCl$_3$) δ ppm 2.36 (s, 3H), 2.60 (t, J=4.8 Hz, 4H), 3.20 (t, J=4.8 Hz, 4H), 3.78 (s, 3H), 3.80 (s, 2H), 5.38 (s, 1H), 6.81 (d, J=8.0 Hz, 2H), 6.90 (d, J=8.4 Hz, 2H), 7.03 (d, J=8.4 Hz, 2H), 7.08 (d, J=8.8 Hz, 2H), 7.21 (d, J=2.0 Hz, 1H), 7.68 (d, J=2.0 Hz, 1H), 7.88 (d, J=4.0 Hz, 1H), 9.88 (s, 1H); MS (LC-MS) m/z 432 (M+H)$^+$.

Example 17

3-{[4-(4-methylpiperazin-1-yl)phenyl]amino}-5-(2-naphthylmethyl)pyridine-2-carboxamide

Example 17A 3-bromo-5-(naphthalen-2-ylmethyl)picolinonitrile

EXAMPLE 1A and naphthalen-2-ylmethyl zinc bromide were processed using the method described in EXAMPLE 1B to afford the title compound.

Example 17B

3-{[4-(4-methylpiperazin-1-yl)phenyl]amino}-5-(2-naphthylmethyl)pyridine-2-carboxamide EXAMPLE 17A and 4-(4-methylpiperazin-1-yl)aniline were processed using the method described in EXAMPLE 1C to afford the title compound. $^1$H NMR (CDCl$_3$) δ ppm 2.36 (s, 3H), 2.58 (t, J=4.8, 5.2 Hz, 4H), 3.16 (t, J=4.8, 5.2 Hz, 4H), 4.01 (s, 2H), 5.37 (s, 1H), 6.84 (d, J=8.8 Hz, 2H), 7.05 (d, J=8.0 Hz, 2H), 7.23 (s, 1H), 7.45 (m, 2H), 7.56 (s, 1H), 7.78 (m, 4H), 7.89 (d, J=4.0 Hz, 1H), 9.88 (s, 1H); MS (LC-MS) m/z 452 (M+H)$^+$.

Example 18

5-(3,5-difluorobenzyl)-3-{[4-(4-methylpiperazin-1-yl)phenyl]amino}pyridine-2-carboxamide

Example 18A 3-bromo-5-(3,5-difluorobenzyl)picolinonitrile

EXAMPLE 1A and 3,5-difluorobenzyl zinc bromide were processed using the method described in EXAMPLE 1B to afford the title compound.

Example 18B 5-(3,5-difluorobenzyl)-3-{[4-(4-methylpiperazin-1-yl)phenyl]amino}pyridine-2-carboxamide EXAMPLE 18A and 4-(4-methylpiperazin-1-yl)aniline were processed using the method described in EXAMPLE 1C to afford the title compound. $^1$H NMR (CDCl$_3$) δ ppm 2.37 (s, 3H), 2.60 (t, J=4.8 Hz, 4H), 3.21 (t, J=4.8 Hz, 4H), 3.81 (s, 2H), 5.38 (s, 1H), 6.64 (d, J=8 Hz, 2H), 6.65 (m, 1H), 6.93 (d, J=8 Hz, 2H), 7.09 (d, J=7.1 Hz, 2H), 7.16 (d, J=12.0 Hz, 1H), 7.67 (d, J=2.0 Hz, 1H), 7.89 (d, J=4.0 Hz, 1H), 9.90 (s, 1H); MS (LC-MS) m/z 438 (M+H)$^+$.

Example 19

5-(3,4-difluorobenzyl)-3-{[4-(4-methylpiperazin-1-yl)phenyl]amino}pyridine-2-carboxamide

Example 19A 3-bromo-5-(3,4-difluorobenzyl)picolinonitrile

EXAMPLE 1A and 3,4-difluorobenzyl zinc bromide were processed using the method described in EXAMPLE 1B to afford the title compound.

Example 19B 5-(3,4-difluorobenzyl)-3-{[4-(4-methylpiperazin-1-yl)phenyl]amino}pyridine-2-carboxamide EXAMPLE 19A and 4-(4-methylpiperazin-1-yl) were processed using the method described in EXAMPLE 1C to afford the title compound. $^1$H NMR (CDCl$_3$) δ ppm 2.37 (s, 3H), 2.60 (t, J=4.8, 5.2 Hz, 4H), 3.21 (t, J=4.8, 5.2 Hz, 4H), 3.80 (s, 2H), 5.37 (s, 1H), 6.84 (m, 1H), 6.92 (m, 2H), 7.08 (m, 2H), 7.15 (d, J=2.0 Hz, 1H), 7.66 (d, J=2.0 Hz, 1H), 7.88 (d, J=4.0 Hz, 1H), 9.89 (s, 1H); MS (LC-MS) m/z 438 (M+H)$^+$.

Example 20

5-(2,4-difluorobenzyl)-3-{[4-(4-methylpiperazin-1-yl)phenyl]amino}pyridine-2-carboxamide

Example 20A 3-bromo-5-(2,4-difluorobenzyl)picolinonitrile

EXAMPLE 1A and 2,4-difluorobenzyl zinc bromide were processed using the method described in EXAMPLE 1B to afford the title compound.

Example 20B 5-(2,4-difluorobenzyl)-3-{[4-(4-methylpiperazin-1-yl)phenyl]amino}pyridine-2-carboxamide EXAMPLE 20A and 4-(4-methylpiperazin-1-yl)aniline were processed using the method described in EXAMPLE 1C to afford the title compound. $^1$H NMR (CDCl$_3$) δ ppm 2.38 (s, 3H), 2.62 (t, J=4.4 Hz, 4H), 3.22 (t, J=4.4 Hz, 4H), 3.82 (s, 1H), 5.34 (s, 1H), 6.80 (t, J=8.4, 8.8 Hz, 1H), 6.91 (d, J=8.8 Hz, 2H), 7.04 (m, 1H), 7.08 (d, J=8.8 Hz, 2H), 7.21 (s, 1H), 7.69 (d, J=1.5 Hz, 1H), 7.88 (d, J=4.0 Hz, 1H), 9.89 (s, 1H); MS (LC-MS) m/z 438 (M+H)$^+$.

Example 21

5-(2,5-difluorobenzyl)-3-{[4-(4-methylpiperazin-1-yl)phenyl]amino}pyridine-2-carboxamide

Example 21A 3-bromo-5-(2,5-difluorobenzyl)picolinonitrile

EXAMPLE 1A and 2,5-difluorobenzyl zinc bromide were processed using the method described in EXAMPLE 1B to afford the title compound.

Example 21B 5-(2,5-difluorobenzyl)-3-{[4-(4-methylpiperazin-1-yl)phenyl]amino}pyridine-2-carboxamide EXAMPLE 21A and 4-(4-methylpiperazin-1-yl)aniline were processed using the method described in EXAMPLE 1C to afford the title compound. $^1$H NMR (CDCl$_3$) δ ppm 2.37 (s, 3H), 2.61 (t, J=4.8 Hz, 4H), 3.22 (t, J=4.8 Hz, 4H), 3.84 (s, 2H), 5.35 (s, 1H), 6.77 (m, 1H), 6.87 (m, 1H), 6.92 (d, J=8 Hz, 2H), 6.98 (m, 1H), 7.10 (d, J=8 Hz, 2H), 7.23 (s, J=2.0 Hz, 1H), 7.70 (s, J=1.5 Hz, 1H), 7.89 (d, J=4.0 Hz, 1H), 9.90 (s, 1H); MS (LC-MS) m/z 438 (M+H)$^+$.

Example 22

5-(3-methoxybenzyl)-3-{[4-(4-methylpiperazin-1-yl)phenyl]amino}pyridine-2-carboxamide

Example 22A 3-bromo-5-(3-methoxybenzyl)picolinonitrile

EXAMPLE 1A and 3-methoxybenzyl zinc bromide were processed using the method described in EXAMPLE 1B to afford the title compound.

Example 22B 5-(3-methoxybenzyl)-3-{[4-(4-methylpiperazin-1-yl)phenyl]amino}pyridine-2-carboxamide EXAMPLE 22A and 4-(4-methylpiperazin-1-yl)aniline were processed using the method described in EXAMPLE 1C to afford the title compound. $^1$H NMR (CDCl$_3$) δ ppm 2.36 (s, 3H), 2.60 (t, J=4.4, 4.8 Hz, 4H), 3.15 (t, J=4.4, 5.2 Hz, 4H), 3.76 (s, 3H), 3.76 (s, 2H), 5.55 (s, 1H), 6.65 (s, 1H), 6.73 (m, 2H), 6.92 (d, J=6.8 Hz, 2H), 7.08 (d, J=6.8 Hz, 2H), 7.19 (t, J=7.6, 1.0 Hz, 1H), 7.22 (d, J=2.0 Hz, 1H), 7.70 (d, J=2.0 Hz, 1H), 7.89 (d, J=4.0 Hz, 1H), 9.88 (s, 1H); MS (LC-MS) m/z 432 (M+H)$^+$.

Example 23

5-(2-chlorobenzyl)-3-{[4-(4-methylpiperazin-1-yl)phenyl]amino}pyridine-2-carboxamide

Example 23A 3-bromo-5-(2-chlorobenzyl)picolinonitrile

EXAMPLE 1A and 2-chlorobenzyl zinc bromide were processed using the method described in EXAMPLE 1B to afford the title compound.

Example 23B 5-(2-chlorobenzyl)-3-{[4-(4-methylpiperazin-1-yl)phenyl]amino}pyridine-2-carboxamide EXAMPLE 23A and 4-(4-methylpiperazin-1-yl)aniline were processed using the method described in EXAMPLE 1C to afford the title compound. $^1$H NMR (CDCl$_3$) δ ppm 2.30 (s, 3H), 2.53 (t, J=4.8, 5.2 Hz, 4H), 3.13 (t, J=5.2 Hz, 4H), 3.90 (s, 2H), 5.27 (s, 1H), 6.83 (d, J=5.2 Hz, 2H), 7.03 (d, J=5.2 Hz, 2H), 7.04 (s, 1H), 7.11 (t, J=1.0, 2.0 Hz, 2H), 7.17 (d, J=2.0

Hz, 1H), 7.29 (t, J=2.0, 2.8 Hz, 1H), 7.63 (d, J=2.0 Hz, 1H), 7.81 (d, J=4.0 Hz, 1H), 9.81 (s, 1H); MS (LC-MS) m/z 436 (M+H)$^+$.

Example 24

5-(3-chlorobenzyl)-3-{[4-(4-methylpiperazin-1-yl)phenyl]amino}pyridine-2-carboxamide Example 24A 3-bromo-5-(3-chlorobenzyl)picolinonitrile EXAMPLE 1A and 3-chlorobenzyl zinc bromide were processed using the method described in EXAMPLE 1B to afford the title compound.

Example 24B 5-(3-chlorobenzyl)-3-{[4-(4-methylpiperazin-1-yl)phenyl]amino}pyridine-2-carboxamide EXAMPLE 24A and 4-(4-methylpiperazin-1-yl)aniline were processed using the method described in EXAMPLE 1C to afford the title compound. $^1$H NMR (CDCl$_3$) δ ppm 2.37 (s, 3H), 2.60 (t, J=4.8, 5.2 Hz, 4H), 3.21 (t, J=5.2 Hz, 4H), 3.82 (s, 2H), 5.38 (s, 1H), 6.92 (d, J=4.4 Hz, 2H), 6.99 (d, J=2.4 Hz, 1H), 7.08 (d, J=4.4 Hz, 2H), 7.11 (s, 1H), 7.19 (t, J=2.4, 3.6 Hz, 3H), 7.68 (d, J=2.0 Hz, 1H), 7.88 (d, J=4.0 Hz, 1H), 9.89 (s, 1H); MS (LC-MS) m/z 436 (M+H)$^+$.

Example 25

5-(4-chlorobenzyl)-3-{[4-(4-methylpiperazin-1-yl)phenyl]amino}pyridine-2-carboxamide Example 25A 3-bromo-5-(4-chlorobenzyl)picolinonitrile EXAMPLE 1A and 4-chlorobenzyl zinc bromide were processed using the method described in EXAMPLE 1B to afford the title compound.

Example 25B 5-(4-chlorobenzyl)-3-{[4-(4-methylpiperazin-1-yl)phenyl]amino}pyridine-2-carboxamide EXAMPLE 25A and 4-(4-methylpiperazin-1-yl)aniline were processed using the method described in EXAMPLE 1C to afford the title compound. $^1$H NMR (CDCl$_3$) δ ppm 2.31 (s, 3H), 2.55 (t, J=4.4, 5.2 Hz, 4H), 3.15 (t, J=4.8 Hz, 4H), 3.74 (s, 2H), 5.27 (s, 1H), 6.83 (d, J=9.2 Hz, 2H), 6.98 (t, J=4.8, 7.6 Hz, 1H), 7.09 (d, J=1.5 Hz, 2H), 7.16 (s, 1H), 7.18 (s, 1H), 7.59 (d, J=2.0 Hz, 1H), 7.81 (d, J=4.0 Hz, 1H), 9.81 (s, 1H); MS (LC-MS) m/z 436 (M+H)$^+$.

Example 26

5-(3-methylbenzyl)-3-{[4-(4-methylpiperazin-1-yl)phenyl]amino}pyridine-2-carboxamide Example 26A 3-bromo-5-(3-methylbenzyl)picolinonitrile EXAMPLE 1A and 3-methylbenzyl zinc bromide were processed using the method described in EXAMPLE 1B to afford the title compound.

Example 26B 5-(3-methylbenzyl)-3-{[4-(4-methylpiperazin-1-yl)phenyl]amino}pyridine-2-carboxamide EXAMPLE 26A and 4-(4-methylpiperazin-1-yl)aniline were processed using the method described in EXAMPLE 1C to afford the title compound. $^1$H NMR (CDCl$_3$) δ ppm 2.30 (s, 3H), 2.37 (s, 3H), 2.61 (t, J=6.0 Hz, 4H), 3.21 (t, J=4.8 Hz, 4H), 3.80 (s, 3H), 5.37 (d, J=4.4 Hz, 1H), 6.90 (d, J=7.2 Hz, 2H), 6.92 (d, J=2.0 Hz, 2H), 7.01 (d, J=7.2 Hz, 1H), 7.08 (d, J=8.4 Hz, 2H), 7.16 (t, J=7.6 Hz, 1H), 7.23 (d, J=1.5 Hz, 1H), 7.70 (d, J=2.0 Hz, 1H), 7.88 (d, J=4.0 Hz, 1H), 9.88 (s, 1H); MS (LC-MS) m/z 416 (M+H)$^+$.

Example 27

5-(2-methylbenzyl)-3-{[4-(4-methylpiperazin-1-yl)phenyl]amino}pyridine-2-carboxamide Example 27A 3-bromo-5-(2-methylbenzyl)picolinonitrile EXAMPLE 1A and 2-methylbenzyl zinc bromide were processed using the method described in EXAMPLE 1B to afford the title compound.

Example 27B 5-(2-methylbenzyl)-3-{[4-(4-methylpiperazin-1-yl)phenyl]amino}pyridine-2-carboxamide EXAMPLE 27A and 4-(4-methylpiperazin-1-yl)aniline were processed using the method described in EXAMPLE 1C to afford the title compound. $^1$H NMR (CDCl$_3$) δ ppm 2.22 (s, 3H), 2.36 (s, 3H), 2.61 (t, J=4.8 Hz, 4H), 3.20 (t, J=4.8 Hz, 4H), 3.85 (s, 3H), 5.37 (d, J=3.6 Hz, 1H), 6.88 (d, J=8.4 Hz, 2H), 7.01 (t, J=2.0 Hz, 1H), 7.03 (d, J=8.4 Hz, 2H), 7.12 (m, 4H), 7.64 (d, J=2.0 Hz, 1H), 7.88 (d, J=4.0 Hz, 1H), 9.88 (s, 1H); MS (LC-MS) m/z 416 (M+H)$^+$.

Example 28

5-(2-methoxybenzyl)-3-{[4-(4-methylpiperazin-1-yl)phenyl]amino}pyridine-2-carboxamide Example 28A 3-bromo-5-(2-methoxybenzyl)picolinonitrile EXAMPLE 1A and 2-methoxybenzyl zinc bromide were processed using the method described in EXAMPLE 1B to afford the title compound.

Example 28B 5-(2-methoxybenzyl)-3-{[4-(4-methylpiperazin-1-yl)phenyl]amino}pyridine-2-carboxamide EXAMPLE 28A and 4-(4-methylpiperazin-1-yl)aniline were processed using the method described in EXAMPLE 1C to afford the title compound. $^1$H NMR (CDCl$_3$) δ ppm 2.30 (s, 3H), 2.53 (t, J=4.8 Hz, 4H), 3.13 (t, J=4.8, 5.2 Hz, 4H), 3.69 (s, 3H), 3.75 (s, 2H), 5.28 (s, 1H), 6.78 (m, J=8.0, 8.4 Hz, 2H), 6.82 (d, J=8.0 Hz, 2H), 6.97 (dd, J=1.8, 8.0 Hz, 1H), 7.01 (d, J=8.0 Hz, 2H), 7.10 (td, J=2.0, 8.4 Hz, 1H), 7.22 (s, 1H), 7.66 (d, J=2.0 Hz, 1H), 7.81 (d, J=4.0 Hz, 1H), 9.77 (s, 1H); MS (LC-MS) m/z 432 (M+H)$^+$.

Example 29

5-(4-methylbenzyl)-3-{[4-(4-methylpiperazin-1-yl)phenyl]amino}pyridine-2-carboxamide

Example 29A 3-bromo-5-(4-methylbenzyl)picolinonitrile

EXAMPLE 1A and 4-methylbenzyl zinc bromide were processed using the method described in EXAMPLE 1B to afford the title compound.

Example 29B 5-(4-methylbenzyl)-3-{[4-(4-methylpiperazin-1-yl)phenyl]amino}pyridine-2-carboxamide EXAMPLE 29A and 4-(4-methylpiperazin-1-yl)aniline were processed using the method described in EXAMPLE 1C to afford the title compound. $^1$H NMR (CDCl$_3$) δ ppm 2.23 (s, 3H), 2.30 (s, 3H), 2.54 (t, J=4.8 Hz, 4H), 3.14 (t, J=4.8 Hz, 4H), 3.73 (s, 3H), 5.26 (d, J=3.2 Hz, 1H), 6.84 (dd, J=2.0, 6.4 Hz, 2H), 6.93 (d, J=6.4 Hz, 2H), 7.02 (t, J=2.4, 6.4 Hz, 4H), 7.14 (d, J=2.0 Hz, 1H), 7.62 (d, J=2.0 Hz, 1H), 7.81 (d, J=3.2 Hz, 1H), 9.80 (s, 1H); MS (LC-MS) m/z 416 (M+H)$^+$.

Example 30

5-(2-chloro-6-fluorobenzyl)-3-{[4-(4-methylpiperazin-1-yl)phenyl]amino}pyridine-2-carboxamide

Example 30A 3-bromo-5-(2-chloro-6-fluorobenzyl)picolinonitrile

EXAMPLE 1A and 2-chloro-6-fluorobenzyl zinc bromide were processed using the method described in EXAMPLE 1B to afford the title compound.

Example 30B 5-(2-chloro-6-fluorobenzyl)-3-{[4-(4-methylpiperazin-1-yl)phenyl]amino}pyridine-2-carboxamide EXAMPLE 30A and 4-(4-methylpiperazin-1-yl)aniline were processed using the method described in EXAMPLE 1C to afford the title compound. $^1$H NMR (CDCl$_3$) δ ppm 2.38 (s, 3H), 2.62 (t, J=4.8 Hz, 4H), 3.22 (t, J=4.8 Hz, 4H), 4.03 (d, J=2.0 Hz, 2H), 5.44 (d, J=3.6 Hz, 1H), 6.92 (dd, J=2.0, 6.4 Hz, 2H), 6.99 (m, 1H), 7.09 (dd, J=2.0, 6.4 Hz, 2H), 7.17 (m, 2H), 7.34 (d, J=1.5 Hz, 1H), 7.77 (d, J=1.5 Hz, 1H), 7.88 (d, J=4.0 Hz, 1H), 9.90 (s, 1H); MS (LC-MS) m/z 454 (M+H)$^+$.

Example 31

5-(2,6-dichlorobenzyl)-3-{[4-(4-methylpiperazin-1-yl)phenyl]amino}pyridine-2-carboxamide

Example 31A 3-bromo-5-(2,6-dichlorobenzyl)picolinonitrile

EXAMPLE 1A and 2,6-dichlorobenzyl zinc bromide were processed using the method described in EXAMPLE 1B to afford the title compound.

Example 31B 5-(2,6-dichlorobenzyl)-3-{[4-(4-methylpiperazin-1-yl)phenyl]amino}pyridine-2-carboxamide EXAMPLE 31A and 4-(4-methylpiperazin-1-yl)aniline were processed using the method described in EXAMPLE 1C to afford the title compound. $^1$H NMR (CDCl$_3$) δ ppm 2.38 (s, 3H), 2.63 (t, J=4.8 Hz, 4H), 3.21 (t, J=4.8 Hz, 4H), 4.20 (s, 2H), 5.42 (d, J=5.0 Hz, 1H), 6.92 (dd, J=2.0, 6.8 Hz, 2H), 7.09 (dd, J=2.0, 6.8 Hz, 2H), 7.13 (t, J=1.0, 7.0 Hz, 1H), 7.29 (t, J=3.0, 10.0 Hz, 3H), 7.73 (d, J=2.0 Hz, 1H), 7.88 (d, J=4.5 Hz, 1H), 9.88 (s, 1H); MS (LC-MS) m/z 470 (M+H)$^+$.

Example 32

5-(biphenyl-2-ylmethyl)-3-{[4-(4-methylpiperazin-1-yl)phenyl]amino}pyridine-2-carboxamide

Example 32A 3-bromo-5-(biphenyl-2-methyl)picolinonitrile

EXAMPLE 1A and biphenyl-2-methyl zinc bromide were processed using the method described in EXAMPLE 1B to afford the title compound.

Example 32B 5-(biphenyl-2-ylmethyl)-3-{[4-(4-methylpiperazin-1-yl)phenyl]amino}pyridine-2-carboxamide EXAMPLE 32A and 4-(4-methylpiperazin-1-yl)aniline were processed using the method described in EXAMPLE 1C to afford the title compound. $^1$H NMR (CDCl$_3$) δ ppm 2.34 (s, 3H), 2.59 (s, 4H), 3.17 (t, J=4.8 Hz, 4H), 3.75 (s, 2H), 5.25 (s, 1H), 6.84 (d, J=8.0 Hz, 2H), 6.88 (s, 1H), 6.93 (d, J=8.0 Hz, 2H), 7.10 (m, 3H), 7.15 (m, 1H), 7.21 (m, 2H), 7.25 (m, 2H), 7.26 (m, 1H), 7.41 (d, J=2.0 Hz, 1H), 7.78 (d, J=4.0 Hz, 1H), 9.75 (s, 1H); MS (LC-MS) m/z 478 (M+H)$^+$.

Example 33

3-{[4-(4-methylpiperazin-1-yl)phenyl]amino}-5-[3-(trifluoromethyl)benzyl]pyridine-2-carboxamide

Example 33A 3-bromo-5-(3-trifluoromethylbenzyl)picolinonitrile

EXAMPLE 1A and 3-trifluoromethylbenzyl zinc bromide were processed using the method described in EXAMPLE 1B to afford the title compound.

Example 33B

3-{[4-(4-methylpiperazin-1-yl)phenyl]amino}-5-[3-(trifluoromethyl)benzyl]pyridine-2-carboxamide EXAMPLE 33A and 4-(4-methylpiperazin-1-yl)aniline were processed using the method described in EXAMPLE 1C to afford the title compound. $^1$H NMR (CDCl$_3$) δ ppm 2.87 (s, 3H), 3.21 (m, J=2.0, 4.5 Hz, 8H), 3.91 (s, 2H), 6.90 (m, J=3.5, 8.5 Hz, 2H), 7.09 (m, J=2.0, 7.6 Hz, 2H), 7.11 (d, J=2.0 Hz, 1H), 7.37 (m, 4H), 7.73 (d, J=2.0 Hz, 1H); MS (LC-MS) m/z 470 (M+H)$^+$.

Example 34

5-[1-(3-fluorophenyl)ethyl]-3-{[4-(4-methylpiperazin-1-yl)phenyl]amino}pyridine-2-carboxamide

Example 34A 3-bromo-5-(1-(3-fluorophenyl)ethyl)picolinonitrile

EXAMPLE 14A and iodomethane were processed using the method described in EXAMPLE 2A to afford the title compound.

Example 34B

5-[1-(3-fluorophenyl)ethyl]-3-{[4-(4-methylpiperazin-1-yl)phenyl]amino}pyridine-2-carboxamide EXAMPLE 34A and 4-(4-methylpiperazin-1-yl)aniline were processed using the method described in EXAMPLE 1C to afford the title compound. $^1$H NMR (CDCl$_3$) δ ppm 9.89 (s, 1H), 7.90-7.84 (m, 1H), 7.70 (d, J=1.8, 1H), 7.28-7.19 (m, 3H), 7.11-7.04 (m, 2H), 6.97-6.83 (m, 5H), 4.03 (q, J=7.2, 1H), 3.24-3.18 (m, 4H), 2.64-2.57 (m, 4H), 2.37 (s, 3H), 1.56 (d, J=7.2, 3H); MS (ESI) m/z 434 (M+H)$^+$.

Example 35

5-[2-(3-fluorophenyl)propan-2-yl]-3-{[4-(4-methylpiperazin-1-yl)phenyl]amino}pyridine-2-carboxamide

Example 35A 3-bromo-5-(2-(3-fluorophenyl)propan-2-yl)picolinonitrile

EXAMPLE 34A and iodomethane were processed using the method described in EXAMPLE 2A to afford the title compound.

Example 35B

5-[2-(3-fluorophenyl)propan-2-yl]-3-{[4-(4-methylpiperazin-1-yl)phenyl]amino}pyridine-2-carboxamide EXAMPLE 35A and 4-(4-methylpiperazin-1-yl)aniline were processed using the method described in EXAMPLE 1C to afford the title compound. $^1$H NMR (CDCl$_3$) δ ppm 9.89 (s, 1H), 7.87 (s, 1H), 7.66 (d, J=2.0, 1H), 7.33 (d, J=2.0, 1H), 7.27 (m, 1H), 7.06 (d, J=8.8, 2H), 6.94-6.86 (m, 5H), 5.44 (s, 1H), 3.25-3.15 (m, 4H), 2.66-2.56 (m, 4H), 2.37 (s, 3H), 1.61 (s, 6H); MS (ESI) m/z 448 (M+H)$^+$.

Example 36

3-{[3-chloro-4-(4-methylpiperazin-1-yl)phenyl]amino}-5-[1-(3-fluorophenyl)ethyl]pyridine-2-carboxamide EXAMPLE 34A and 3-chloro-4-(4-methylpiperazin-1-yl)aniline were processed using the method described in EXAMPLE 1C to afford the title compound. $^1$H NMR (CDCl$_3$) δ ppm 10.05 (s, 1H), 7.90 (s, 1H), 7.79 (d, J=1.8, 1H), 7.36-7.25 (m, 2H), 7.20 (t, J=12.6, 1H), 7.10-6.83 (m, 5H), 5.36 (s, 1H), 4.17-4.02 (m, 1H), 3.09 (s, 4H), 2.66 (s, 4H), 2.40 (s, 3H), 1.61 (d, J=7.2, 3H); MS (ESI) m/z 468 (M+H)$^+$.

Example 37

5-[1-(3-fluorophenyl)ethyl]-3-{[2-methoxy-4-(4-methylpiperazin-1-yl)phenyl]amino}pyridine-2-carboxamide EXAMPLE 34A and 2-methoxy-4-(4-methylpiperazin-1-yl)aniline were processed using the method described in EXAMPLE 1C to afford the title compound. $^1$H NMR (CDCl$_3$) δ ppm 9.79 (s, 1H), 7.89-7.77 (m, 1H), 7.70 (d, J=1.9, 1H), 7.23-7.19 (m, 1H), 7.19-7.07 (m, 2H), 6.95 (d, J=7.8, 1H), 6.93-6.83 (m, 2H), 6.54 (d, J=2.6, 1H), 6.48 (dd, J=8.5, 2.6, 1H), 5.32-5.26 (s, 1H), 4.04 (q, J=7.2, 1H), 3.31-3.20 (m, 4H), 2.68-2.60 (m, 4H), 2.40 (s, 3H), 1.55 (s, 3H); MS (ESI) m/z 464 (M+H)$^+$.

Example 38

5-(2,6-dichlorobenzyl)-3-{[2-methoxy-4-(4-methylpiperazin-1-yl)phenyl]amino}pyridine-2-carboxamide EXAMPLE 1B and 2-methoxy-4-(4-methylpiperazin-1-yl)aniline were processed using the method described in EXAMPLE 1C to afford the title compound. $^1$H NMR (DMSO-d$_6$) δ ppm 2.69 (s, 3H), 3.13 (br, 4H), 3.38 (br, 4H), 3.69 (s, 3H), 4.20 (s, 2H), 6.47 (dd, 1H, J=2.4 Hz, J=8.4 Hz), 6.65 (d, 1H, J=2.4 Hz), 6.90 (s, 1H), 7.01 (d, 1H, J=8.4 Hz), 7.35 (t, 1H, J=8.0 Hz), 7.49-7.51 (m, 3H), 7.75 (d, 1H, J=2.4 Hz), 8.07 (d, 1H, J=2.4 Hz); MS (ESI) m/z 501 (M+H)$^+$.

Example 39

5-(2,6-dichlorobenzyl)-3-{[4-(piperazin-1-yl)phenyl]amino}pyridine-2-carboxamide

Example 39A tert-butyl 4-(4-(2-carbamoyl-5-(2,6-dichlorobenzyl)pyridin-3-ylamino)phenyl)piperazine-1-carboxylate EXAMPLE 1B and tert-butyl 4-(4-amino-phenyl)piperazine-1-carboxylate were processed using the method described in EXAMPLE 1C to afford the title compound.

Example 39B

5-(2,6-dichlorobenzyl)-3-{[4-(piperazin-1-yl)phenyl]amino}pyridine-2-carboxamide EXAMPLE 39B was processed using the method described in EXAMPLE 1D to afford the title compound. $^1$H NMR (DMSO-$d_6$) δ ppm 3.18 (br, 4H), 3.25 (m, 4H), 4.22 (s, 2H), 6.94 (d, 2H, J=8.8 Hz), 7.03 (d, 2H, J=8.8 Hz), 7.17 (s, 1H), 7.34 (t, 1H, J=8.0 Hz), 7.51 (d, 2H, J=8.0 Hz), 7.59 (s, 3H), 7.76 (s, 1H), 8.12 (s, 1H), 10.18 (s, 1H); MS (ESI) m/z 457 (M+H)$^+$.

Example 40

5-(2-chloro-5-fluorobenzyl)-3-{[3-chloro-4-(4-methylpiperazin-1-yl)phenyl]amino}pyridine-2-carboxamide

Example 40A

3-bromo-5-(2-chloro-5-fluorobenzyl)picolinonitrile

EXAMPLE 1A and 2-chloro-5-fluorobenzyl zinc bromide were processed using the method described in EXAMPLE 1B to afford the title compound.

Example 40B

5-(2-chloro-5-fluorobenzyl)-3-{[3-chloro-4-(4-methylpiperazin-1-yl)phenyl]amino}pyridine-2-carboxamide EXAMPLE 40A and 3-chloro-4-(4-methylpiperazin-1-yl)aniline were processed using the method described in EXAMPLE 1C to afford the title compound. $^1$H NMR (CDCl$_3$) δ ppm 10.12 (s, 1H), 7.95-7.89 (s, 1H), 7.81 (d, J=1.8, 1H), 7.36 (dd, J=8.8, 5.1, 1H), 7.31 (d, J=1.7, 1H), 7.20 (s, 1H), 7.06-7.02 (s, 2H), 6.93 (td, J=8.3, 3.0, 1H), 6.87 (dd, J=8.9, 3.0, 1H), 5.43-5.37 (m, 1H), 4.00 (s, 2H), 3.48-3.28 (m, 4H), 2.73-2.68 (m, 4H), 1.28-1.23 (s, 3H); MS (ESI) m/z 489 (M+H)$^+$.

Example 41

5-(2-chloro-5-fluorobenzyl)-3-{[2-methoxy-4-(piperazin-1-yl)phenyl]amino}pyridine-2-carboxamide

Example 41B

5-(2-chloro-5-fluorobenzyl)-3-{[2-methoxy-4-(piperazin-1-yl)phenyl]amino}pyridine-2-carboxamide EXAMPLE 40A and 2-methoxy-4-(4-methylpiperazin-1-yl)aniline were processed using the method described in EXAMPLE 1C to afford the title compound. $^1$H NMR (CDCl$_3$) δ ppm 9.80 (s, 1H), 7.89 (s, 1H), 7.71 (d, J=1.4, 1H), 7.32 (dd, J=8.8, 5.2, 1H), 7.12 (d, J=8.5, 1H), 7.06 (s, 1H), 6.89 (d, J=2.9, 1H), 6.80 (dd, J=9.1, 2.9, 1H), 6.56-6.43 (m, 2H), 5.41 (s, 1H), 3.94 (s, 2H), 3.76 (s, 3H), 3.33-3.06 (m, 8H); MS (ESI) m/z 470 (M+H)$^+$.

Example 42

5-(2-chloro-6-fluorobenzyl)-3-{[2-methoxy-4-(piperazin-1-yl)phenyl]amino}pyridine-2-carboxamide

Example 42A tert-butyl 4-(4-(2-carbamoyl-5-(2-chloro-6-fluorobenzyl)pyridin-3-ylamino)-3-methoxyphenyl)piperazine-1-carboxylate EXAMPLE 30A and tert-butyl 4-(4-amino-3-methoxyphenyl)piperazine-1-carboxylate were processed using the method described in EXAMPLE 1C to afford the title compound.

Example 42B

5-(2-chloro-6-fluorobenzyl)-3-{[2-methoxy-4-(piperazin-1-yl)phenyl]amino}pyridine-2-carboxamide EXAMPLE 42A was processed using the method described in EXAMPLE 1D to afford the title compound. $^1$H NMR (CDCl$_3$) δ ppm 9.79 (s, 1H), 7.87 (d, J=4.2, 1H), 7.77 (d, J=1.8, 1H), 7.22-7.10 (m, 4H), 7.06-6.94 (m, 1H), 6.54 (d, J=2.5, 1H), 6.48 (dd, J=8.5, 2.6, 1H), 5.30 (s, 1H), 4.03 (d, J=2.1, 2H), 3.77 (s, 3H), 3.21-3.05 (m, 8H); MS (ESI) m/z 470 (M+H)$^+$.

Example 43

5-(2-chloro-6-fluorobenzyl)-3-[(2-methoxy-4-{4-[2-(morpholin-4-yl)ethyl]piperazin-1-yl}phenyl)amino]pyridine-2-carboxamide A solution of EXAMPLE 42B (25 mg, 0.053 mmol) in tetrahydrofuran (1 mL), triethylamine (22.24 uL, 0.16 mmol) and 4-(2-chloroethyl)morpholine hydrochloride (9.9 mg, 0.053 mmol) were heated to 75° C. over 18 hours. The reaction mixture was concentrated under reduced pressure and purified on RP-HPLC (10 mM ammonium acetate/acetonitrile) to afford the title compound. $^1$H NMR (CDCl$_3$) δ ppm 9.76 (s, 1H), 7.88 (s, 1H), 7.76 (s, 1H), 7.23-7.06 (m, 4H), 7.06-6.91 (m, 1H), 6.58-6.53 (d, J=2.5, 6H), 6.47 (dd, J=8.6, 2.5, 5H), 5.46 (s, 1H), 4.02 (d, J=1.9, 2H), 3.83-3.68 (m, 7H), 3.27-3.09 (m, 4H), 2.77-2.49 (m, 12H); MS (ESI) m/z 584 (M+H)$^+$.

Example 44

5-(2-chloro-6-fluorobenzyl)-3-[(4-{4-[2-(diethylamino)ethyl]piperazin-1-yl}-2-methoxyphenyl)amino]pyridine-2-carboxamide EXAMPLE 42B and 2-chloro-N,N-diethylethanamine hydrochloride were processed using the method described in EXAMPLE 43 to afford the title compound. $^1$H NMR (CDCL$_3$) δ ppm 9.77 (s, 1H), 7.89-7.83 (m, 1H), 7.76 (s, 1H), 7.20-7.08 (m, 4H), 7.02-6.93 (m, 1H), 6.53 (d, J=2.5, 1H), 6.47 (dd, J=8.5, 2.6, 1H), 5.35-5.28 (m, 1H), 4.02 (d, J=2.1, 2H), 3.76 (s, 3H), 3.24-3.13 (m, 4H), 2.77-2.57 (m, 12H), 1.09 (t, J=7.1, 6H); MS (ESI) m/z 570 (M+H)$^+$.

Example 45

5-(2-chloro-6-fluorobenzyl)-3-({4-[4-(2-hydroxy-2-methylpropyl)piperazin-1-yl]-2-methoxyphenyl}amino)pyridine-2-carboxamide EXAMPLE 42B and 1-chloro-2-methylpropan-2-ol were processed using the method described in EXAMPLE 43 to afford the title compound. $^1$H NMR (CDCl$_3$) δ ppm 9.78 (s, 1H), 7.89-7.83 (m, 1H), 7.76 (d, J=1.7, 1H), 7.22-7.09 (m, 4H), 7.02-6.94 (m, 1H), 6.53 (d, J=2.5, 1H), 6.47 (dd, J=8.5, 2.5, 1H), 5.36-5.30 (m, 1H), 4.03 (d, J=2.1, 2H), 3.77 (s, 3H), 3.24-3.10 (m, 4H), 2.87-2.81 (m, 4H), 2.42 (s, 2H), 1.21 (s, 6H); MS (ESI) m/z 543 (M+H)$^+$.

Example 46

5-(2-chloro-6-fluorobenzyl)-3-{[2-methoxy-4-(4-methylpiperazin-1-yl)phenyl]amino}pyridine-2-carboxamide EXAMPLE 42B and iodomethane were processed using the method described in EXAMPLE 43 to afford the title compound. $^1$H NMR (CDCl$_3$) δ ppm 9.77 (s, 1H), 7.87 (s, 1H), 7.76 (s, 1H), 7.15 (ddd, J=15.0, 10.2, 7.0, 4H), 7.06-6.91 (m, 1H), 6.58-6.42 (m, 2H), 5.42 (s, 1H), 4.03 (d, J=2.0, 2H), 3.77 (s, 3H), 3.29-3.18 (m, 4H), 2.73-2.59 (m, 4H), 2.40 (s, 3H); MS (ESI) m/z 484 (M+H)$^+$.

Example 47

5-(2-chloro-6-fluorobenzyl)-3-{[4-(4-ethylpiperazin-1-yl)-2-methoxyphenyl]amino}pyridine-2-carboxamide EXAMPLE 42B and iodoethane were processed using the method described in EXAMPLE 43 to afford the title compound. $^1$H NMR (CDCl$_3$) δ ppm 9.77 (s, 1H), 7.89-7.83 (m, 1H), 7.76 (s, 1H), 7.21-7.09 (m, 4H), 7.05-6.93 (m, 1H), 6.54 (d, J=2.5, 1H), 6.48 (dd, J=8.5, 2.6, 1H), 5.29 (d, J=4.2, 1H), 4.03 (d, J=2.1, 2H), 3.77 (s, 3H), 3.27-3.20 (m, 4H), 2.69-2.64 (m, 4H), 2.56-2.45 (m, 2H), 1.20-1.12 (m, 3H); MS (ESI) m/z 498 (M+H)$^+$.

Example 48

5-(2-chloro-3,6-difluorobenzyl)-3-{[2-methoxy-4-(piperazin-1-yl)phenyl]amino}pyridine-2-carboxamide

Example 48A 3-bromo-5-(2-chloro-4,6-difluorobenzyl)picolinonitrile

EXAMPLE 1A and 5-chloro-2,4-difluorobenzyl zinc bromide were processed using the method described in EXAMPLE 1B to afford the title compound.

Example 48B tert-butyl 4-(4-(2-carbamoyl-5-(2-chloro-3,6-difluorobenzyl)pyridin-3-ylamino)-3-methoxyphenyl)piperazine-1-carboxylate EXAMPLE 48A and tert-butyl 4-(4-amino-3-methoxyphenyl)piperazine-1-carboxylate were processed using the method described in EXAMPLE 1C to afford the title compound.

Example 48C 5-(2-chloro-3,6-difluorobenzyl)-3-{[2-methoxy-4-(piperazin-1-yl)phenyl]amino}pyridine-2-carboxamide EXAMPLE 48B was processed using the method described in EXAMPLE 1D to afford the title compound. $^1$H NMR (DMSO) δ ppm 9.94 (bs, 1H), 8.07 (bs, 1H), 7.77 (d, J=1.8, 1H), 7.51 (s, 1H), 7.44 (td, J=8.9, 4.9, 1H), 7.33 (td, J=9.1, 4.4, 1H), 7.05 (d, J=8.6, 1H), 6.93 (s, 1H), 6.68 (d, J=2.4, 1H), 6.51 (dd, J=8.6, 2.5, 1H), 4.09-4.04 (m, 2H), 3.69 (s, 3H), 3.38 (m, 4H), 3.24 (m, 4H); MS (ESI) m/z 488 (M+H)$^+$.

Example 49

5-(2-methylphenyl)-3-{[4-(4-methylpiperazin-1-yl)phenyl]amino}pyridine-2-carboxamide

Example 49A 5-bromo-3-fluoropicolinonitrile

A solution of 5-bromo-3-nitropicolinonitrile (6.84 g, 30 mmol) in dimethylsulfoxide was cooled to −25° C. and treated with 1M tetra-n-butylammonium fluoride in tetrahydrofuran (60 mL, 60 mmol). The reaction mixture was stirred at ambient temperature for 1 hour. It was quenched with water and extracted with ethyl acetate. The combined organic layers were dried (Na$_2$SO$_4$), filtered and concentrated to provide crude title compound.

Example 49B 5-bromo-3-(4-(4-methylpiperazin-1-yl)phenylamino)picolinamide

A solution of EXAMPLE 49A (1.8 g, 8.96 mmol) and 4-(4-methylpiperazin-1-yl)aniline (1.713 g, 8.96 mmol) in t-butanol (10 mL) was treated with triethylamine (1.87 mL, 13.43 mmol) was subjected to microwave irradiation (Biotage, Initiator) at 190° C. for 1.5 hours. The reaction mixture was concentrated and purified on silica gel with 0-10% methanol in dichloromethane. The collected material was taken into t-butanol (5 mL), treated with sodium t-butoxide (1.73 g, 18 mmol), and the reaction mixture was stirred at 90° C. for 2 hours. The mixture was concentrated and purified on silica gel with 3-13% methanol in dichloromethane to afford the title compound.

Example 49C 5-(2-methylphenyl)-3-{[4-(4-methylpiperazin-1-yl)phenyl]amino}pyridine-2-carboxamide A solution of EXAMPLE 49B (21.5 mg, 0.055 mmol) and o-tolyl boronic acid (9 mg, 0.066 mmol) in dioxane (3 mL) was treated with an aqueous solution of cesium carbonate (0.11 mL, 0.11 mmol) and [1,1'-bis(diphenylphosphino)ferrocene]dichloropalladium(II) dichloromethane (4.5 mg, 0.005 mmol) and subjected to microwave irradiation (Biotage, Initiator) at 150° C. for 30 minutes. After cooling, the reaction mixture was transferred to a pre-packed column of Si-Carbonate (2 g, 0.79 mmol/g) and eluted with methanol. The column was then washed several times. The solution thus obtained was concentrated under reduced pressure and purified by RP-HPLC (10 mM ammonium acetate/acetonitrile) to provide the title compound as the trifluoroacetate salt. $^1$H NMR (pyridine-$d_5$) δ ppm 11.03 (s, 1H), 8.10 (d, J=1.8, 1H), 7.35-7.25 (m, 8H), 7.01-6.95 (m, 3H), 4.22-4.17 (m, 2H), 3.97-3.93 (m, 2H), 3.85 (s, 3H), 3.64-3.52 (m, 4H), 2.25 (s, 3H); MS (ESI) m/z 402 (M+H)$^+$.

Example 50

5-(2-fluorophenyl)-3-{[4-(4-methylpiperazin-1-yl)phenyl]amino}pyridine-2-carboxamide EXAMPLE 49B and 2-fluorophenyl boronic acid were processed using the method described in EXAMPLE 49C to afford the title compound as the trifluoroacetate salt. $^1$H NMR (pyridine-$d_5$) δ ppm 11.03 (s, 1H), 8.33 (t, J=1.8, 1H), 7.84 (t, J=1.6, 1H), 7.5-7.45 (m, 1H), 7.35-7.28 (m, 3H), 7.25-7.15 (m, 1H) 7.03-6.96 (m, 2H), 4.22-4.17 (m, 2H), 3.97-3.93 (m, 2H), 3.84 (s, 3H), 3.64-3.52 (m, 4H); MS (ESI) m/z 406 (M+H)$^+$.

Example 51

5-(3-fluorophenyl)-3-{[4-(4-methylpiperazin-1-yl)phenyl]amino}pyridine-2-carboxamide EXAMPLE 49B and 3-fluorophenyl boronic acid were processed using the method described in EXAMPLE 49C to afford the title compound as the trifluoroacetate salt. $^1$H NMR (pyridine-$d_5$) δ ppm 11.09 (s, 1H), 8.41 (d, J=1.9, 1H), 7.85 (d, J=1.9, 1H), 7.53-7.49 (m, 1H), 7.46-7.32 (m, 5H), 7.20-7.15 (m, 1H), 7.05-6.99 (m, 2H), 4.22-4.17 (m, 2H), 3.97-3.93 (m, 2H), 3.85 (s, 3H), 3.64-3.52 (m, 4H); MS (ESI) m/z 406 (M+H)$^+$.

Example 52

5-(3-chlorophenyl)-3-{[4-(4-methylpiperazin-1-yl)phenyl]amino}pyridine-2-carboxamide EXAMPLE 49B and 3-fluorophenyl boronic acid were processed using the method described in EXAMPLE 49C to afford the title compound as the trifluoroacetate salt. $^1$H NMR (pyridine-$d_5$) δ ppm 11.10 (s, 1H), 8.38 (d, J=1.9, 1H), 7.84-7.74 (m, 2H), 7.55-7.25 (m, 6H), 7.08-6.97 (m, 2H), 4.22-4.17 (m, 2H), 3.97-3.93 (m, 2H), 3.85 (s, 3H), 3.64-3.52 (m, 4H); MS (ESI) m/z 422 (M+H)$^+$.

Example 53

5-(3-carbamoylphenyl)-3-{[4-(4-methylpiperazin-1-yl)phenyl]amino}pyridine-2-carboxamide EXAMPLE 49B and 3-aminocarbonylphenyl boronic acid were processed using the method described in EXAMPLE 49C to afford the title compound as the trifluoroacetate salt. $^1$H NMR (pyridine-$d_5$) δ ppm 11.09 (s, 1H), 8.99 (bs, 2H), 8.69-8.64 (m, 1H), 8.51-8.35 (m, 2H), 7.90 (d, J=1.9, 1H), 7.75 (m, 1H), 7.58 (m, 1H), 7.31 (s, 2H), 7.01-6.94 (m, 2H), 4.22-4.17 (m, 2H), 3.97-3.93 (m, 2H), 3.85 (s, 3H), 3.64-3.52 (m, 4H); MS (ESI) m/z 431 (M+H)$^+$.

Example 54

3-{[4-(4-methylpiperazin-1-yl)phenyl]amino}-5-{3-[(methylsulfonyl)amino]phenyl}pyridine-2-carboxamide EXAMPLE 49B and 3-methylsulfonamidophenyl boronic acid were processed using the method described in EXAMPLE 49C to afford the title compound as the trifluoroacetate salt. $^1$H NMR (pyridine-$d_5$) δ ppm 11.7 (bs, 1H), 11.06 (s, 1H), 8.97 (d, J=3.5, 1H), 8.43 (d, J=1.9, 1H), 7.92 (t, J=1.8, 1H), 7.86 (d, J=1.9, 1H), 7.74-7.67 (m, 1H), 7.49 (d, J=7.7, 1H), 7.45 (d, J=3.1, 1H), 7.36-7.29 (m, 2H), 7.03-6.96 (m, 2H), 4.22-4.17 (m, 2H), 3.97-3.93 (m, 2H), 3.85 (s, 3H), 3.64-3.52 (m, 4H), 3.25 (s, 3H); MS (ESI) m/z 481 (M+H)$^+$.

Example 55

3-{[4-(4-methylpiperazin-1-yl)phenyl]amino}-5-{2-[(methylsulfonyl)amino]phenyl}pyridine-2-carboxamide EXAMPLE 49B and 2-methylsulfonamidophenyl boronic acid were processed using the method described in EXAMPLE 49C to afford the title compound as the trifluoroacetate salt. $^1$H NMR (pyridine-$d_5$) δ ppm 11.50 (s, 1H), 10.94 (s, 1H), 8.33 (d, J=1.8, 1H), 8.03-7.85 (m, 3H), 7.72-7.60 (m, 1H), 7.50-7.26 (m, 6H), 7.06-6.90 (m, 2H), 4.16 (d, J=11.3, 2H), 4.01-3.87 (m, 2H), 3.84 (s, 3H), 3.56 (d, J=2.3, 4H), 3.17 (s, 3H); MS (ESI) m/z 481 (M+H)$^+$.

Example 56

3-{[4-(4-methylpiperazin-1-yl)phenyl]amino}-5-[(E)-2-phenylvinyl]pyridine-2-carboxamide EXAMPLE 49B and (E)-styrylboronic acid were processed using the method described in EXAMPLE 49C to afford the title compound. $^1$H NMR (DMSO) δ ppm 10.23 (s, 1H), 8.22 (d, J=1.7, 1H), 8.18-8.12 (m, 1H), 7.66-7.56 (m, 3H), 7.49 (d, J=1.7, 1H), 7.44-7.20 (m, 5H), 7.18-7.11 (m, 2H), 7.02-6.96 (m, 2H), 3.17-3.11 (m, 4H), 2.48-2.42 (m, 4H), 2.24 (s, 3H); MS (ESI) m/z 414 (M+H)$^+$.

Example 57

3-{[2-methoxy-4-(4-methylpiperazin-1-yl)phenyl]amino}-5-{3-[(methylsulfonyl)amino]phenyl}pyridine-2-carboxamide Example 57A 5-bromo-3-(2-methoxy-4-(4-methylpiperazin-1-yl)phenylamino)picolinamide EXAMPLE 49A and 2-methoxy-4-(4-methylpiperazin-1-yl)aniline were processed using the method described in EXAMPLE 49B to afford the title compound.

Example 57B

3-[2-methoxy-4-(4-Methyl-piperazin-1-yl)-phenylamino]-5-(3-(methylsulfonamido)phenyl)-pyridine-2-carboxamide EXAMPLE 57A and 3-methylsulfonamidophenyl boronic acid were processed using the method described in EXAMPLE 49C to afford the title compound. $^1$H NMR (DMSO) δ ppm 10.03 (s, 1H), 8.16 (d, J=2.6, 1H), 8.09 (d, J=1.8, 1H), 7.58 (d, J=3.7, 1H), 7.44 (t, J=7.9, 1H), 7.34 (dd, J=9.0, 4.7, 2H), 7.26 (t, J=5.0, 2H), 7.19 (d, J=8.6, 1H), 6.68 (d, J=2.5, 1H), 6.52 (dd, J=8.7, 2.5, 1H), 4.10 (s, 1H), 3.79 (s, 3H), 3.19-3.11 (m, 8H), 3.02 (s, 3H), 2.24 (s, 3H); MS (ESI) m/z 512 (M+H)$^+$.

Example 58

5-(2-chlorophenyl)-3-{[4-(4-methylpiperazin-1-yl) phenyl]amino}pyridine-2-carboxamide EXAMPLE 49B and 2-chlorophenyl boronic acid were processed using the method described in EXAMPLE 49C to afford the title compound. $^1$H NMR (pyridine-$d_5$) δ ppm 11.01 (s, 1H), 9.00-8.95 (m, 1H), 8.17 (d, J=1.8, 1H), 7.73 (d, J=1.9, 1H), 7.56-7.50 (m, 1H), 7.42-7.36 (m, 1H), 7.37-7.27 (m, 4H), 6.99-6.93 (m, 2H), 3.36-3.30 (m, 4H), 2.95-2.89 (m, 4H), 2.56-2.48 (s, 3H); MS (ESI) m/z 422 (M+H)$^+$.

Example 59

5-(3-cyanophenyl)-3-{[4-(4-methylpiperazin-1-yl) phenyl]amino}pyridine-2-carboxamide EXAMPLE 49B and 3-cyanophenyl boronic acid were processed using the method described in EXAMPLE 49C to afford the title compound as the trifluoroacetate salt. $^1$H NMR (pyridine-$d_5$) δ ppm 11.09 (s, 1H), 9.06-9.01 (m, 1H), 8.38 (d, J=1.9, 1H), 8.11 (t, J=1.7, 1H), 7.84 (d, J=1.9, 1H), 7.82-7.76 (m, 1H), 7.70 (dt, J=7.7, 1.3, 1H), 7.44 (t, J=7.8, 1H), 7.39-7.33 (m, 2H), 7.01-6.96 (m, 2H), 3.33-3.27 (m, 4H), 2.87-2.81 (m, 4H), 2.52-2.47 (s, 3H); MS (ESI) m/z 413 (M+H)$^+$.

Example 60

5-{[4-(4-methylpiperazin-1-yl)phenyl]amino}-3,3'-bipyridine-6-carboxamide

EXAMPLE 49B and 3-pyridylboronic acid were processed using the method described in EXAMPLE 49C to afford the title compound as the trifluoroacetate salt. $^1$H NMR (pyridine-$d_5$) δ ppm 11.04 (s, 1H), 9.07 (dd, J=2.4, 0.9, 1H), 9.01-8.89 (m, 1H), 8.36 (d, J=1.9, 1H), 7.90-7.83 (m, 1H), 7.82 (d, J=1.9, 1H), 7.40-7.34 (m, 3H), 7.36-7.26 (m, 1H), 7.07-6.98 (m, 2H), 3.31-3.21 (m, 4H), 2.75-2.66 (m, 4H), 2.38 (s, 3H); MS (ESI) m/z 389 (M+H)$^+$.

Example 61

5-(2-cyanophenyl)-3-{[4-(4-methylpiperazin-1-yl) phenyl]amino}pyridine-2-carboxamide EXAMPLE 49B and 2-cyanophenyl boronic acid were processed using the method described in EXAMPLE 49C to afford the title compound as the trifluoroacetate salt. $^1$H NMR (pyridine-$d_5$) δ ppm 11.07 (s, 1H), 8.93 (d, J=23.4, 1H), 8.24 (d, J=1.9, 1H), 7.88-7.77 (m, 2H), 7.55-7.40 (m, 5H), 7.04 (d, J=8.9, 2H), 3.33-3.16 (m, 4H), 2.80-2.62 (m, 4H), 2.40 (s, 3H); MS (ESI) m/z 413 (M+H)$^+$.

Example 62

5-[3-(dimethylcarbamoyl)phenyl]-3-{[4-(4-methylpiperazin-1-yl)phenyl]amino}pyridine-2-carboxamide EXAMPLE 49B and 3-dimethylcarbamoylphenyl boronic acid were processed using the method described in EXAMPLE 49C to afford the title compound as the trifluoroacetate salt. $^1$H NMR (pyridine-$d_5$) δ ppm 11.06 (s, 1H), 9.01-8.96 (m, 1H), 8.41 (d, J=1.9, 1H), 7.96 (t, J=1.7, 1H), 7.88 (d, J=1.9, 1H), 7.65 (dt, J=7.7, 1.4, 1H), 7.45 (t, J=7.6, 1H), 7.35-7.30 (m, 2H), 6.98-6.92 (m, 2H), 3.41-3.29 (m, 4H), 3.15-3.06 (s, 3H), 3.03-2.84 (m, 4H), 2.83-2.77 (m, 3H), 2.56 (s, 3H); MS (ESI) m/z 459 (M+H)$^+$.

Example 63

3-{[4-(4-methylpiperazin-1-yl)phenyl]amino}-5-(1H-pyrazol-4-yl)pyridine-2-carboxamide EXAMPLE 49B and 1H-pyrazol-4-ylboronic acid were processed using the method described in EXAMPLE 49C to afford the title compound as the trifluoroacetate salt. $^1$H NMR (pyridine-$d_5$) δ ppm 11.06-11.00 (m, 1H), 8.94-8.85 (m, 2H), 8.60-8.50 (m, 3H), 8.33 (s, 2H), 7.98-7.91 (m, 1H), 7.43-7.33 (m, 3H), 7.08-6.97 (m, 3H), 3.23-3.16 (m, 4H), 2.60-2.52 (m, 4H), 2.28 (s, 3H); MS (ESI) m/z 378 (M+H)$^+$.

Example 64

3-{[4-(4-methylpiperazin-1-yl)phenyl]amino}-5-(1-methyl-1H-pyrazol-4-yl)pyridine-2-carboxamide EXAMPLE 49B and 1-methyl-1H-pyrazol-4-ylboronic acid were processed using the method described in EXAMPLE 49C to afford the title compound as the trifluoroacetate salt. $^1$H NMR (pyridine-$d_5$) δ ppm 11.03 (s, 1H), 8.89 (d, J=3.4, 1H), 8.59-8.53 (m, 1H), 8.47 (d, J=1.8, 1H), 8.10 (d, J=0.8, 1H), 7.98 (s, 1H), 7.84 (d, J=1.8, 1H), 7.35-7.30 (m, 2H), 7.01-6.96 (m, 2H), 3.80 (s, 3H), 3.35-3.29 (m, 4H), 2.91-2.85 (m, 4H), 2.52 (s, 3H); MS (ESI) m/z 392 (M+H)$^+$.

Example 65

3-{[4-(4-methylpiperazin-1-yl)phenyl]amino}-5-(3-{[(2,2,2-trifluoroethyl)sulfonyl]amino}phenyl)pyridine-2-carboxamide

Example 65A

3-[4-(4-methylpiperazin-1-yl)phenylamino]-5-[3-aminophenyl]pyridine-2-carboxamide EXAMPLE 49B and 3-aminophenyl boronic acid were processed using the method described in EXAMPLE 49C to afford the title compound.

Example 65B

3-{[4-(4-methylpiperazin-1-yl)phenyl]amino}-5-(3-{[(2,2,2-trifluoroethyl)sulfonyl]amino}phenyl)pyridine-2-carboxamide A solution of EXAMPLE 65A (18 mg, 0.045 mmol) in dichloromethane (0.4 mL) and pyridine (0.1 mL) was added to a cooled to 0° C. 2,2,2-trifluoroethanesulfonyl chloride (9 mg, 0.05 mmol). The reaction mixture was stirred slowly warming to ambient temperature over 18 hours and concentrated under reduced pressure. The crude material was purified by RP-HPLC (10 mM ammonium acetate/acetonitrile) to afford the title compound. $^1$H NMR (DMSO-$d_6$) δ ppm 10.27 (s, 1H), 8.21 (d, J=3.0, 1H), 8.14 (d, J=1.9, 1H), 7.68-7.63 (m, 1H), 7.52-7.40 (m, 2H), 7.40-7.33 (m, 2H), 7.30-7.23 (m, 1H), 7.20-7.14 (m, 2H), 7.00-6.94 (m, 2H), 4.54 (q, J=9.8, 2H), 3.13 (m, 4H), 2.45 (m, 4H), 2.24 (s, 3H); MS (ESI) m/z 549 (M+H)$^+$.

Example 66

5-{3-[(cyclopropylsulfonyl)amino]phenyl}-3-{[4-(4-methylpiperazin-1-yl)phenyl]amino}pyridine-2-carboxamide EXAMPLE 65A and cyclopropanesulfonyl chloride were processed using the method described in EXAMPLE 65B to afford the title compound. $^1$H NMR (DMSO-d$_6$) δ ppm 10.25 (s, 1H), 8.21 (d, J=2.3, 1H), 8.13 (d, J=1.9, 1H), 7.65 (d, J=2.4, 1H), 7.47 (d, J=1.9, 1H), 7.45-7.36 (m, 2H), 7.36-7.24 (m, 2H), 7.17 (d, J=8.9, 2H), 6.97 (d, J=8.9, 2H), 3.14-3.10 (m, 4H), 2.63 (s, 1H), 2.48-2.44 (m, 4H), 2.22 (s, 3H), 0.90 (dd, J=6.2, 3.7, 4H); MS (ESI) m/z 507 (M+H)$^+$.

Example 67

5-(3-{[(5-methyl-1,2-oxazol-4-yl)sulfonyl]amino}phenyl)-3-{[4-(4-methylpiperazin-1-yl)phenyl]amino}pyridine-2-carboxamide EXAMPLE 65A and 5-methylisoxazole-4-sulfonyl chloride were processed using the method described in EXAMPLE 65B to afford the title compound. $^1$H NMR (DMSO-d$_6$) δ ppm 10.30 (s, 1H), 8.24 (s, 1H), 8.15 (d, J=1.8, 1H), 7.63 (s, 1H), 7.50 (d, J=1.7, 1H), 7.30 (dd, J=11.0, 4.7, 2H), 7.20 (t, J=9.7, 3H), 7.16-7.08 (m, 2H), 7.05-7.01 (m, 2H), 1.91 (s, 3H), 1.74 (s, 3H); MS (ESI) m/z 548 (M+H)$^+$.

Example 68

3-{[4-(4-methylpiperazin-1-yl)phenyl]amino}-5-{3-[(2-thienylsulfonyl)amino]phenyl}pyridine-2-carboxamide EXAMPLE 65A and thiophene-2-sulfonyl chloride were processed using the method described in EXAMPLE 65B to afford the title compound. $^1$H NMR (DMSO-d$_6$) δ ppm 10.22 (s, 1H), 8.22-8.17 (m, 1H), 8.05 (d, J=1.9, 1H), 7.81 (d, J=5.1, 1H), 7.67-7.62 (m, 1H), 7.48 (dd, J=3.7, 1.3, 1H), 7.40-7.33 (m, 2H), 7.34-7.27 (m, 1H), 7.26 (bs, 1H), 7.20-7.13 (m, 3H), 7.07-7.01 (m, 1H), 7.03-6.97 (m, 2H), 3.20-3.10 (m, 4H), 2.45 (m, 4H), 2.22 (s, 3H), 1.91 (s, 1H); MS (ESI) m/z 549 (M+H)$^+$.

Example 69

3-{[4-(4-methylpiperazin-1-yl)phenyl]amino}-5-(3-{[(1-methyl-1H-pyrazol-3-yl)sulfonyl]amino}phenyl)pyridine-2-carboxamide EXAMPLE 65A and 1-methyl-1H-pyrazole-3-sulfonyl chloride were processed using the method described in EXAMPLE 65B to afford the title compound. $^1$H NMR (CDCl$_3$) δ ppm 9.95 (s, 1H), 8.00 (d, J=1.9, 1H), 7.97-7.92 (m, 1H), 7.44 (d, J=1.9, 1H), 7.34-7.24 (m, 3H), 7.26-7.20 (m, 2H), 7.22-7.14 (m, 3H), 6.95 (d, 2H), 6.58 (d, J=2.3, 1H), 5.46-5.40 (m, 1H), 3.88 (s, 3H), 3.27-3.21 (m, 4H), 2.63 (m, 4H), 2.38 (s, 3H), 2.09 (s, 1H); MS (ESI) m/z 547 (M+H)$^+$.

Example 70

5-anilino-3-{[4-(4-methylpiperazin-1-yl)phenyl]amino}pyridine-2-carboxamide

Example 70A 5-bromo-3-(4-(4-methylpiperazin-1-yl)phenylamino)picolinonitrile A solution of 5-bromo-3-fluoropicolinonitrile (1 g, 5 mmol), from EXAMPLE 49A, and 4-(4-methylpiperazin-1-yl)aniline (1.24 g, 6.5 mmol) in isopropanol (15 mL) was treated with triethylamine (0.76 mL, 7.5 mmol) was subjected to microwave irradiation (Biotage, Initiator) at 180° C. for 2 hours. The reaction mixture was concentrated and purified on silica gel with 2-25% methanol in dichloromethane to afford the title compound.

Example 70B 5-anilino-3-{[4-(4-methylpiperazin-1-yl)phenyl]amino}pyridine-2-carboxamide Aniline (22.4 mg, 0.24 mmol), cesium carbonate (91 mg, 0.28 mmol), palladium (II) acetate (2.25 mg, 0.01 mmol) and (±)-2,2'-bis(diphenylphosphino)-1,1'-binaphthalene (9.34 mg, 0.015 mmol) were added to a dry microwave vial. The vial was capped and purged with nitrogen. A degassed solution of EXAMPLE 70A (74.5 mg, 0.2 mmol) in toluene (1 mL) was added to the microwave vial and the reaction was stirred at 110° C. for 3 hours. The reaction mixture was concentrated and purified on silica gel with 2-25% methanol in dichloromethane to afford 3-[4-(4-methyl-piperazin-1-yl)-phenylamino]-5-phenylamino-pyridine-2-carbonitrile. A solution of this (20 mg, 0.052 mmol) in dimethylsulfoxide was treated with potassium carbonate (36 mg, 0.26 mmol) and 30% hydrogen peroxide (1 mL) while keeping temperature below 0° C. The reaction mixture was stirred at 0° C. for 1 hour and then at room temperature for 18 hours. The reaction was quenched by the addition water, filtered, washed with water and dried to provide the title compound. $^1$H NMR (DMSO-d$_6$) δ ppm 10.15 (s, 1H), 8.64 (s, 1H), 7.83-7.78 (m, 1H), 7.65 (d, J=2.3, 1H), 7.26 (t, J=7.7, 2H), 7.21 (d, J=3.4, 1H), 7.11-7.04 (m, 4H), 6.96-6.88 (m, 4H), 3.12-3.04 (m, 4H), 2.42-2.32 (m, 4H), 2.20 (s, 3H); MS (ESI) m/z 402 (M+H)$^+$.

Example 71

5-{[2-(dimethylsulfamoyl)phenyl]amino}-3-{[4-(4-methylpiperazin-1-yl)phenyl]amino}pyridine-2-carboxamide EXAMPLE 70A and 2-amino-N,N-dimethylbenzenesulfonamide were processed using the method described in EXAMPLE 70B to afford the title compound. $^1$H NMR (DMSO-d$_6$) δ ppm 10.33 (s, 1H), 8.09 (s, 1H), 7.95 (d, J=16.4, 1H), 7.84-7.68 (m, 2H), 7.67-7.50 (m, 2H), 7.38 (s, 1H), 7.30-7.12 (m, 3H), 7.12-6.95 (m, 4H), 2.89 (dd, J=20.4, 7.4, 4H), 2.66 (dt, J=9.5, 4.8, 2H), 2.61 (s, 6H), 2.54 (s, 3H), 2.33 (dd, J=3.6, 1.8, 2H); MS (ESI) m/z 510 (M+H)$^+$.

Example 72

Enzyme Inhibition Data

The following procedure is used to determine ALK Activity.

ALK kinase assays were conducted with the indicated final concentrations unless otherwise specified. In 384 well black plates (Axygen), 8 μl of compound (2% DMSO) was incubated with 8 μl Lck-peptide substrate (0.5 μM, biotin-Ahx-GAEEEIYAAFFA-COOH) and 8 μl of a mixture of ALK (3 nM, Millipore) and ATP (50 μM) in reaction buffer (50 mM Hepes, pH 7.4; 10 mM MgCl$_2$; 2 mM MnCl$_2$; 0.1 mM sodium orthovanadate; 0.01% BSA and 1 mM DTT (added fresh before assay) for 1 h at room temperature. Reactions were then quenched by the addition of 30 μl quench solution (streptavidin-allophycocyanin and Europium-cryptate PT66 monoclonal antibody in 40 mM Hepes, pH 7.4; 480 mM KF; 66 mM EDTA; 0.01% Tween-20; and 0.1% BSA) at room temperature. Plates were read 1 h after quenching on an Envision Multilaber Reader and $IC_{50}$ values were calculated using a sigmoidal fit of the concentration/inhibition response curves. These values were converted to apparent $K_i$ values using the Cheng-Prusoff relationship.

Alternatively, 4 nM ALK (Millipore) and 50 μM ATP were pre-incubated for 30 min at room temperate in 384 well plates (Corning 3676) in 2.5× reaction buffer (125 nM SEB from Cisbio Bioassays, 12.5 mM $MgCl_2$, 5 mM $MnCl_2$, and 2.5 mM DTT). Reactions were initiated by the addition of 4 μl ALK-ATP mixture to 2 μl compounds (2% DMSO) and 4 μl TK-substrate biotin (Cisbio Bioassays). After incubation for 1 h at room temperature, reactions were quenched in 10 μl stop buffer (Cisbio detection buffer containing Streptavididn-XL665 and Eu-Cryptate PT66 monoclonal antibody). Plates were read 1 h after quenching on an Envision Multilaber Reader and $IC_{50}$ values were calculated using a sigmoidal fit of the concentration/inhibition response curves. These values were converted to apparent $K_i$ values using the Cheng-Prusoff relationship. Results are shown in Table 1 A correlates to an $K_i$=<100 nM, B correlates to an $K_i$ between 100 nM and 1 μM, C correlates to an $K_i$=>1 μM.

TABLE 1

| ALK Activity | |
|---|---|
| Example | HTRF_ALK Human-$K_i$ |
| 1 | A |
| 2 | A |
| 3 | B |
| 4 | B |
| 5 | B |
| 6 | B |
| 7 | B |
| 8 | C |
| 9 | B |
| 10 | B |
| 11 | B |
| 12 | B |
| 13 | A |
| 14 | A |
| 15 | A |
| 16 | B |
| 17 | C |
| 18 | A |
| 19 | B |
| 20 | B |
| 21 | A |
| 22 | B |
| 23 | B |
| 24 | B |
| 25 | C |
| 26 | B |
| 27 | C |
| 28 | B |
| 29 | B |
| 30 | A |
| 31 | A |
| 32 | B |
| 33 | B |
| 34 | B |
| 35 | B |
| 36 | B |
| 37 | B |
| 38 | A |
| 39 | A |
| 40 | B |
| 41 | A |
| 42 | A |

TABLE 1-continued

| ALK Activity | |
|---|---|
| Example | HTRF_ALK Human-$K_i$ |
| 43 | B |
| 44 | A |
| 45 | B |
| 46 | B |
| 47 | A |
| 48 | B |
| 49 | B |
| 50 | B |
| 51 | C |
| 52 | C |
| 53 | B |
| 54 | A |
| 55 | B |
| 56 | C |
| 57 | B |
| 58 | B |
| 59 | C |
| 60 | C |
| 61 | C |
| 62 | B |
| 63 | C |
| 64 | C |
| 65 | B |
| 66 | B |
| 67 | B |
| 68 | A |
| 69 | B |
| 70 | B |
| 71 | B |

Compounds of the present invention assessed by the above-described assays were found to have ALK kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:
1. A compound of formula (I):

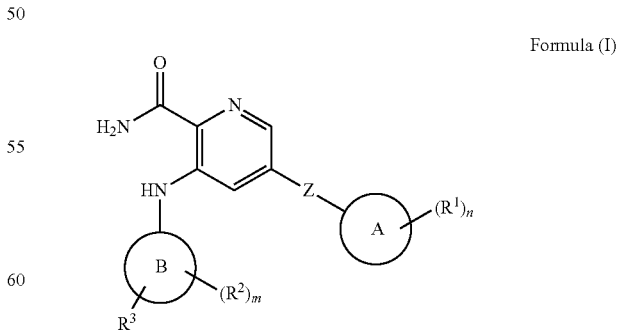

Formula (I)

wherein
A is phenyl, naphthyl, indenyl, $C_{3-8}$ cycloalkyl, 5-7 membered heterocycloalkyl, 5-7 membered heterocycloalkenyl, or 5-7 membered heteroaryl;

B is phenyl, pyridinyl, pyrimidinyl, pyrazinyl, pyridazinyl, or pyrazolinyl;

Z is bond, $C_{1-6}$ alkylene, $C_{2-6}$ alkenylene, —O—, or —(NR$^4$)—;

$R^1$, at each occurrence, is independently selected from the group consisting of halo, CN, NO$_2$, $C_{1-6}$-alkyl, $C_{1-6}$-haloalkyl, aryl, $C_{3-8}$ cycloalkyl, heteroaryl, heterocycloalkyl, OR$^5$, SR$^5$, C(O)R$^5$, C(O)NR$^6$R$^7$, C(O)OR$^5$, OC(O)R$^5$, OC(O)NR$^6$R$^7$, NR$^6$R$^7$, NR$^6$C(O)R$^5$, S(O)R$^5$, S(O)NR$^6$R$^7$, S(O)$_2$R$^5$, NR$^6$S(O)$_2$R$^5$, and S(O)$_2$NR$^6$R$^7$; wherein the $C_{3-8}$ cycloalkyl, aryl, heterocycloalkyl, and heteroaryl are optionally substituted with 1, 2, or 3 substituents independently selected from halo, $C_{1-4}$ alkyl, $C_{1-4}$ haloalkyl, CN, NO$_2$, OR$^a$, SR$^a$, C(O)R$^a$, C(O)NR$^b$R$^c$, C(O)OR$^a$, OC(O)R$^a$, OC(O)NR$^b$R$^c$, NR$^b$R$^c$, NR$^b$C(O)R$^a$, S(O)R$^a$, S(O)NR$^b$R$^c$, S(O)$_2$R$^a$, NR$^b$S(O)$_2$R$^a$, and S(O)$_2$NR$^b$R$^c$;

$R^2$, at each occurrence, is independently selected from the group consisting of halo, CN, OH, $C_{1-4}$ alkyl, $C_{1-4}$-haloalkyl, $C_{1-4}$ alkoxy, $C_{1-4}$ haloalkoxy, $C_{1-4}$-thioalkoxy, amino, $C_{1-4}$ alkylamino, and $C_{1-4}$ dialkylamino;

$R^3$ is selected from the group consisting of aryl, $C_{3-8}$ cycloalkyl, heteroaryl, heterocycloalkyl, aryl-$C_{1-6}$-alkyl-, $C_{3-8}$ cycloalkyl-$C_{1-6}$-alkyl-, heteroaryl-$C_{1-6}$-alkyl-, heterocycloalkyl-$C_{1-6}$-alkyl-, OR$^8$, C(O)R$^8$, C(O)NR$^9$R$^{10}$, C(O)OR$^8$, OC(O)R$^8$, OC(O)NR$^9$R$^{10}$, NR$^9$R$^{10}$, NR$^9$C(O)R$^8$, S(O)R$^8$, S(O)NR$^9$R$^{10}$, S(O)$_2$R$^8$, NR$^9$S(O)$_2$R$^8$, and S(O)$_2$NR$^9$R$^{10}$, wherein the $C_{3-8}$ cycloalkyl, aryl, heterocycloalkyl, and heteroaryl, alone or part of another moiety, are optionally substituted with one, two, or three R$^{11}$;

$R^4$ is H or $C_{1-6}$-alkyl;

$R^5$, $R^6$, and $R^7$, at each occurrence, are independently selected from H, $C_{1-6}$ alkyl, $C_{1-6}$ haloalkyl, aryl, $C_{3-8}$ cycloalkyl, heteroaryl, and heterocycloalkyl, wherein the aryl, $C_{3-8}$ cycloalkyl, heteroaryl, and heterocycloalkyl moiety is optionally substituted with halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, C(O)C$_{1-4}$ alkyl, C(O)NH$_2$, C(O)NH(C$_{1-4}$ alkyl), or C(O)N(C$_{1-4}$ alkyl)$_2$;

$R^8$, $R^9$, and $R^{10}$, at each occurrence, are independently selected from H, $C_{1-6}$ alkyl, $C_{1-6}$ haloalkyl, heteroaryl-$C_{1-6}$-alkyl-, heterocycloalkyl-$C_{1-6}$-alkyl-, R$^{12}$R$^{13}$N—$C_{1-6}$-alkyl-, aryl, $C_{3-8}$ cycloalkyl, heteroaryl, and heterocycloalkyl, wherein the aryl, $C_{3-8}$ cycloalkyl, heteroaryl, and heterocycloalkyl, alone or as part of another moeity, is optionally substituted with halo, CN, OH, $C_{1-4}$ alkyl, $C_{1-4}$-haloalkyl, $C_{1-4}$ alkoxy, $C_{1-4}$ haloalkoxy, amino, $C_{1-4}$ alkylamino, $C_{1-4}$ dialkylamino, C(O)OH, C(O)C$_{1-4}$ alkyl, C(O)NH$_2$, C(O)NH(C$_{1-4}$ alkyl), or C(O)N(C$_{1-4}$ alkyl)$_2$;

$R^{11}$ is selected from the group consisting of halo, $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, hydroxy-$C_{1-4}$-alkyl-, $C_{1-4}$ alkyl-$C_{1-4}$alkoxy, aryl, $C_{3-8}$ cycloalkyl, heteroaryl, heterocycloalkyl, aryl-(C$_{1-2}$ alkyl)-, $C_{3-8}$ cycloalkyl-(C$_{1-2}$ alkyl)-, heteroaryl-(C$_{1-2}$ alkyl)-, heterocycloalkyl-(C$_{1-2}$ alkyl)-, CN, NO$_2$, OR$^d$, SR$^d$, C(O)R$^d$, C(O)NR$^e$R$^f$, C(O)OR$^d$, OC(O)R$^d$, OC(O)NR$^e$R$^f$, NR$^e$R$^f$, NR$^e$C(O)R$^d$, S(O)R$^d$, S(O)NR$^e$R$^f$, S(O)$_2$R$^d$, NR$^e$S(O)$_2$R$^d$, and S(O)$_2$NR$^e$R$^f$, wherein the aryl, $C_{3-8}$ cycloalkyl, heteroaryl, and heterocycloalkyl, alone or as part of another moiety, are optionally substituted with one, two or three substituents independently selected from halo and $C_{1-4}$ alkyl;

$R^{12}$ and $R^{13}$, at each occurrence, are independently selected from the group consisting of H, $C_{1-6}$ alkyl, $C_{1-6}$ haloalkyl, aryl, $C_{3-8}$ cycloalkyl, heteroaryl, and heterocycloalkyl;

$R^a$ is selected from the group consisting of H, $C_{1-6}$ alkyl, $C_{1-6}$ haloalkyl, aryl, $C_{3-8}$ cycloalkyl, heteroaryl, and heterocycloalkyl;

$R^b$ and $R^c$ are independently selected from the group consisting of H, $C_{1-6}$ alkyl, $C_{1-6}$ haloalkyl, aryl, $C_{3-8}$ cycloalkyl, heteroaryl, heterocycloalkyl;

$R^d$ is selected from the group consisting of H, $C_{1-6}$ alkyl, $C_{1-6}$ haloalkyl, aryl, $C_{3-8}$ cycloalkyl, heteroaryl, and heterocycloalkyl;

$R^e$ and $R^f$ are independently selected from the group consisting of H, $C_{1-6}$ alkyl, $C_{1-6}$ haloalkyl, aryl, $C_{3-8}$ cycloalkyl, heteroaryl, and heterocycloalkyl;

m is 0, 1, 2, or 3; and n is 0, 1, 2, or 3;

or a pharmaceutically acceptable salt or solvate thereof.

2. The compound of claim 1 of formula (I) wherein Z is —CH$_2$—, —CH$_2$CH$_{2-5}$—CH(CH$_3$)—, or —C(CH$_3$)$_2$—.

3. The compound of claim 1 of formula (I) wherein Z is —C(=CH$_2$)— or —CH=CH—.

4. The compound of claim 1 of formula (I) wherein Z is a bond.

5. The compound of claim 1 of formula (I) wherein A is phenyl.

6. The compound of claim 5 of formula (I) wherein n is 0, 1, or 2; and $R^1$ is halo, OR$^5$, $C_{1-6}$ alkyl, $C_{1-6}$ haloalkyl, or CN.

7. The compound of claim 5 of formula (I) wherein n is 1, $R^1$ is C(O)NR$^6$R$^7$, C(O)OR$^5$, NR$^6$C(O)R$^5$, NR$^6$S(O)$_2$R$^5$, or S(O)$_2$NR$^6$R$^7$.

8. The compound of claim 1 of formula (I) wherein A is a 5-7 membered heteroaryl selected from the group consisting of include furanyl, thiophenyl, pyrrolyl, imidazolyl, pyrazoyl, triazolyl, tetrazolyl, oxazolyl, isoxazolyl, thiazolyl, isothiazolyl, thiodiazolyl, oxadiazolyl, oxatriazolyl, dioxazolyl, oxathiazolyl, oxathiolyl, pyridinyl, pyridazinyl, pyrimidinyl, and pyrazinyl.

9. The compound of claim 1 of formula (I) wherein B is phenyl.

10. The compound of claim 1 of formula (I) wherein $R^3$ is heterocycloalkyl.

11. The compound of claim 1 of formula (I) wherein B is

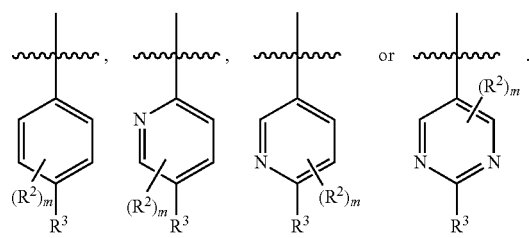

12. The compound of claim 10 of formula (I) wherein
m is 0 or 1;
R² is halo, $C_{1-4}$ alkyl, or $C_{1-4}$ alkoxy;
R³ is

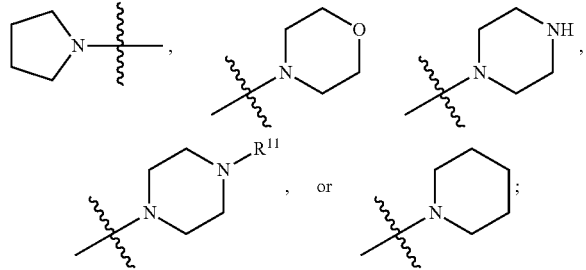

and
R¹¹ is $C_{1-4}$ alkyl, $C_{1-4}$ haloalkyl, amino-$C_{1-4}$-alkyl-, $C_{1-4}$ alkylamino-$C_{1-4}$ alkyl-, $C_{1-4}$ dialkylamino-$C_{1-4}$ alkyl-, and hydroxy-$C_{1-4}$-alkyl-, $C_{1-4}$ alkyl-$C_{1-4}$ alkoxy, aryl, $C_{3-8}$ cycloalkyl, heteroaryl, heterocycloalkyl, aryl-($C_{1-2}$ alkyl)-, $C_{3-8}$ cycloalkyl-($C_{1-2}$ alkyl)—, heteroaryl-($C_{1-2}$ alkyl)-, or heterocycloalkyl-($C_{1-2}$ alkyl)-, wherein the aryl, $C_{3-8}$ cycloalkyl, heteroaryl, and heterocycloalkyl, alone or as part of another moiety, are optionally substituted with 1, 2, or 3 substituents independently selected from halo and $C_{1-4}$ alkyl.

13. The compound of claim 1 of formula (I) or a salt or a solvate thereof selected from the group consisting of
5-(2,6-dichlorobenzyl)-3-{[2-methoxy-4-(piperazin-1-yl)phenyl]amino}pyridine-2-carboxamide;
5-[1-(2,6-dichlorophenyl)ethyl]-3-{[2-methoxy-4-(piperazin-1-yl)phenyl]amino}pyridine-2-carboxamide;
5-benzyl-3-{[4-(4-methylpiperazin-1-yl)phenyl]amino}pyridine-2-carboxamide;
5-benzyl-3-{[3-(4-methylpiperazin-1-yl)phenyl]amino}pyridine-2-carboxamide;
5-(cyclohexylmethyl)-3-{[4-(4-methylpiperazin-1-yl)phenyl]amino}pyridine-2-carboxamide;
3-{[4-(4-methylpiperazin-1-yl)phenyl]amino}-5-phenylpyridine-2-carboxamide;
5-benzyl-3-{[3-chloro-4-(4-methylpiperazin-1-yl)phenyl]amino}pyridine-2-carboxamide;
5-benzyl-3-{[3-methyl-4-(4-methylpiperazin-1-yl)phenyl]amino}pyridine-2-carboxamide;
5-benzyl-3-{[2-methyl-4-(4-methylpiperazin-1-yl)phenyl]amino}pyridine-2-carboxamide;
3-{[4-(4-methylpiperazin-1-yl)phenyl]amino}-5-(1-phenylvinyl)pyridine-2-carboxamide;
3-{[4-(4-methylpiperazin-1-yl)phenyl]amino}-5-(1-phenylethyl)pyridine-2-carboxamide;
5-(4-fluorobenzyl)-3-{[4-(4-methylpiperazin-1-yl)phenyl]amino}pyridine-2-carboxamide;
5-(2-fluorobenzyl)-3-{[4-(4-methylpiperazin-1-yl)phenyl]amino}pyridine-2-carboxamide;
5-(3-fluorobenzyl)-3-{[4-(4-methylpiperazin-1-yl)phenyl]amino}pyridine-2-carboxamide;
5-(2,6-difluorobenzyl)-3-{[4-(4-methylpiperazin-1-yl)phenyl]amino}pyridine-2-carboxamide;
5-(4-methoxybenzyl)-3-{[4-(4-methylpiperazin-1-yl)phenyl]amino}pyridine-2-carboxamide;
3-{[4-(4-methylpiperazin-1-yl)phenyl]amino}-5-(2-naphthylmethyl)pyridine-2-carboxamide;
5-(3,5-difluorobenzyl)-3-{[4-(4-methylpiperazin-1-yl)phenyl]amino}pyridine-2-carboxamide;
5-(3,4-difluorobenzyl)-3-{[4-(4-methylpiperazin-1-yl)phenyl]amino}pyridine-2-carboxamide;
5-(2,4-difluorobenzyl)-3-{[4-(4-methylpiperazin-1-yl)phenyl]amino}pyridine-2-carboxamide;
5-(2,5-difluorobenzyl)-3-{[4-(4-methylpiperazin-1-yl)phenyl]amino}pyridine-2-carboxamide;
5-(3-methoxybenzyl)-3-{[4-(4-methylpiperazin-1-yl)phenyl]amino}pyridine-2-carboxamide;
5-(2-chlorobenzyl)-3-{[4-(4-methylpiperazin-1-yl)phenyl]amino}pyridine-2-carboxamide;
5-(3-chlorobenzyl)-3-{[4-(4-methylpiperazin-1-yl)phenyl]amino}pyridine-2-carboxamide;
5-(4-chlorobenzyl)-3-{[4-(4-methylpiperazin-1-yl)phenyl]amino}pyridine-2-carboxamide;
5-(3-methylbenzyl)-3-{[4-(4-methylpiperazin-1-yl)phenyl]amino}pyridine-2-carboxamide;
5-(2-methylbenzyl)-3-{[4-(4-methylpiperazin-1-yl)phenyl]amino}pyridine-2-carboxamide;
5-(2-methoxybenzyl)-3-{[4-(4-methylpiperazin-1-yl)phenyl]amino}pyridine-2-carboxamide;
5-(4-methylbenzyl)-3-{[4-(4-methylpiperazin-1-yl)phenyl]amino}pyridine-2-carboxamide;
5-(2-chloro-6-fluorobenzyl)-3-{[4-(4-methylpiperazin-1-yl)phenyl]amino}pyridine-2-carboxamide;
5-(2,6-dichlorobenzyl)-3-{[4-(4-methylpiperazin-1-yl)phenyl]amino}pyridine-2-carboxamide;
5-(biphenyl-2-ylmethyl)-3-{[4-(4-methylpiperazin-1-yl)phenyl]amino}pyridine-2-carboxamide;
3-{[4-(4-methylpiperazin-1-yl)phenyl]amino}-5-[3-(trifluoromethyl)benzyl]pyridine-2-carboxamide;
5-[1-(3-fluorophenyl)ethyl]-3-{[4-(4-methylpiperazin-1-yl)phenyl]amino}pyridine-2-carboxamide;
5-[2-(3-fluorophenyl)propan-2-yl]-3-{[4-(4-methylpiperazin-1-yl)phenyl]amino}pyridine-2-carboxamide;
3-{[3-chloro-4-(4-methylpiperazin-1-yl)phenyl]amino}-5-[1-(3-fluorophenyl)ethyl]pyridine-2-carboxamide;
5-[1-(3-fluorophenyl)ethyl]-3-{[2-methoxy-4-(4-methylpiperazin-1-yl)phenyl]amino}pyridine-2-carboxamide;
5-(2,6-dichlorobenzyl)-3-{[2-methoxy-4-(4-methylpiperazin-1-yl)phenyl]amino}pyridine-2-carboxamide;
5-(2,6-dichlorobenzyl)-3-{[4-(piperazin-1-yl)phenyl]amino}pyridine-2-carboxamide;
5-(2-chloro-5-fluorobenzyl)-3-{[3-chloro-4-(4-methylpiperazin-1-yl)phenyl]amino}pyridine-2-carboxamide;
5-(2-chloro-5-fluorobenzyl)-3-{[2-methoxy-4-(piperazin-1-yl)phenyl]amino}pyridine-2-carboxamide;
5-(2-chloro-6-fluorobenzyl)-3-{[2-methoxy-4-(piperazin-1-yl)phenyl]amino}pyridine-2-carboxamide;
5-(2-chloro-6-fluorobenzyl)-3-[(2-methoxy-4-{4-[2-(morpholin-4-yl)ethyl]piperazin-1-yl}phenyl)amino]pyridine-2-carboxamide;
5-(2-chloro-6-fluorobenzyl)-3-[(4-{4-[2-(diethylamino)ethyl]piperazin-1-yl}-2-methoxyphenyl)amino]pyridine-2-carboxamide;
5-(2-chloro-6-fluorobenzyl)-3-({4-[4-(2-hydroxy-2-methylpropyl)piperazin-1-yl]-2-methoxyphenyl}amino)pyridine-2-carboxamide;
5-(2-chloro-6-fluorobenzyl)-3-{[2-methoxy-4-(4-methylpiperazin-1-yl)phenyl]amino}pyridine-2-carboxamide;
5-(2-chloro-6-fluorobenzyl)-3-{[4-(4-ethylpiperazin-1-yl)-2-methoxyphenyl]amino}pyridine-2-carboxamide;
5-(2-chloro-3,6-difluorobenzyl)-3-{[2-methoxy-4-(piperazin-1-yl)phenyl]amino}pyridine-2-carboxamide;

5-(2-methylphenyl)-3-{[4-(4-methylpiperazin-1-yl)phenyl]amino}pyridine-2-carboxamide;
5-(2-fluorophenyl)-3-{[4-(4-methylpiperazin-1-yl)phenyl]amino}pyridine-2-carboxamide;
5-(3-fluorophenyl)-3-{[4-(4-methylpiperazin-1-yl)phenyl]amino}pyridine-2-carboxamide;
5-(3-chlorophenyl)-3-{[4-(4-methylpiperazin-1-yl)phenyl]amino}pyridine-2-carboxamide;
5-(3-carbamoylphenyl)-3-{[4-(4-methylpiperazin-1-yl)phenyl]amino}pyridine-2-carboxamide;
3-{[4-(4-methylpiperazin-1-yl)phenyl]amino}-5-{3-[(methylsulfonyl)amino]phenyl}pyridine-2-carboxamide;
3-{[4-(4-methylpiperazin-1-yl)phenyl]amino}-5-{2-[(methylsulfonyl)amino]phenyl}pyridine-2-carboxamide;
3-{[4-(4-methylpiperazin-1-yl)phenyl]amino}-5-[(E)-2-phenylvinyl]pyridine-2-carboxamide;
3-{[2-methoxy-4-(4-methylpiperazin-1-yl)phenyl]amino}-5-{3-[(methylsulfonyl)amino]phenyl}pyridine-2-carboxamide;
5-(2-chlorophenyl)-3-{[4-(4-methylpiperazin-1-yl)phenyl]amino}pyridine-2-carboxamide;
5-(3-cyanophenyl)-3-{[4-(4-methylpiperazin-1-yl)phenyl]amino}pyridine-2-carboxamide;
5-{[4-(4-methylpiperazin-1-yl)phenyl]amino}-3,3'-bipyridine-6-carboxamide;
5-(2-cyanophenyl)-3-{[4-(4-methylpiperazin-1-yl)phenyl]amino}pyridine-2-carboxamide;
5-[3-(dimethylcarbamoyl)phenyl]-3-{[4-(4-methylpiperazin-1-yl)phenyl]amino}pyridine-2-carboxamide;
3-{[4-(4-methylpiperazin-1-yl)phenyl]amino}-5-(1H-pyrazol-4-yl)pyridine-2-carboxamide;
3-{[4-(4-methylpiperazin-1-yl)phenyl]amino}-5-(1-methyl-1H-pyrazol-4-yl)pyridine-2-carboxamide;
3-{[4-(4-methylpiperazin-1-yl)phenyl]amino}-5-(3-{[(2,2,2-trifluoroethyl)sulfonyl]amino}phenyl)pyridine-2-carboxamide;
5-{3-[(cyclopropylsulfonyl)amino]phenyl}-3-{[4-(4-methylpiperazin-1-yl)phenyl]amino}pyridine-2-carboxamide;
5-(3-{[(5-methyl-1,2-oxazol-4-yl)sulfonyl]amino}phenyl)-3-{[4-(4-methylpiperazin-1-yl)phenyl]amino}pyridine-2-carboxamide;
3-{[4-(4-methylpiperazin-1-yl)phenyl]amino}-5-{3-[(2-thienylsulfonyl)amino]phenyl}pyridine-2-carboxamide;
3-{[4-(4-methylpiperazin-1-yl)phenyl]amino}-5-(3-{[(1-methyl-1H-pyrazol-3-yl)sulfonyl]amino}phenyl)pyridine-2-carboxamide;
5-anilino-3-{[4-(4-methylpiperazin-1-yl)phenyl]amino}pyridine-2-carboxamide; and
5-{[2-(dimethylsulfamoyl)phenyl]amino}-3-{[4-(4-methylpiperazin-1-yl)phenyl]amino}pyridine-2-carboxamide.

14. A pharmaceutical composition comprising a compound or pharmaceutically acceptable salt of claim 1 and pharmaceutically acceptable excipient.

15. A method of inhibiting ALK in a mammal comprising administering thereto a therapeutically acceptable amount of a compound or pharmaceutically acceptable salt of claim 1.

* * * * *

UNITED STATES PATENT AND TRADEMARK OFFICE
CERTIFICATE OF CORRECTION

PATENT NO.       : 8,859,546 B2
APPLICATION NO.  : 13/354556
DATED            : October 14, 2014
INVENTOR(S)      : Vasudevan et al.

It is certified that error appears in the above-identified patent and that said Letters Patent is hereby corrected as shown below:

In the Claims

Column 67, line 51, claim 1: "moeity" to read as -- moiety --

Column 68, line 26, claim 2: "$-CH_2CH_{2\text{-}5}-CH(CH_3)-$" to read as -- $-CH_2CH_2-, -CH(CH_3)-$ --

Column 68, line 45, claim 8: "pyrazoyl" to read as -- pyrazolyl --

Signed and Sealed this
First Day of September, 2015

Michelle K. Lee
*Director of the United States Patent and Trademark Office*